(12) United States Patent
Klein et al.

(10) Patent No.: US 6,673,541 B1
(45) Date of Patent: Jan. 6, 2004

(54) DNA AMPLIFICATION OF A SINGLE CELL

(75) Inventors: Christoph Klein, Munich (DE); Oleg Schmidt-Kittler, Munich (DE)

(73) Assignee: Micromet AG, Martinsried (DE)

(*) Notice: Subject to any disclaimer, the term of this patent is extended or adjusted under 35 U.S.C. 154(b) by 0 days.

(21) Appl. No.: 09/787,505

(22) PCT Filed: Sep. 17, 1999

(86) PCT No.: PCT/EP99/06912
§ 371 (c)(1),
(2), (4) Date: Jun. 18, 2001

(87) PCT Pub. No.: WO00/17390
PCT Pub. Date: Mar. 30, 2000

(30) Foreign Application Priority Data

Sep. 18, 1998 (EP) .............................................. 98117799
Sep. 19, 1998 (EP) .............................................. 98117745

(51) Int. Cl.$^7$ ........................... C12Q 1/68; C12P 19/34; C07H 21/02; C07H 21/04; C07H 19/00

(52) U.S. Cl. .......................... 435/6; 435/7.1; 435/91.1; 435/91.2; 536/22.1; 536/23.1; 536/24.3; 536/24.31; 536/24.32; 536/24.33

(58) Field of Search ................... 435/6, 91.2; 536/23.1, 536/24.3

(56) References Cited

U.S. PATENT DOCUMENTS 6,258,539 B1 * 7/2001 Hunkapiller et al. ........... 435/6
6,380,370 B1 * 4/2002 Doucette-Stamm et al. ..... 536/23.1

FOREIGN PATENT DOCUMENTS

EP          0 735 144          10/1996

OTHER PUBLICATIONS

Zhang et al., "Whole Genome Amplification From A Single Cell: Implications For Genetic Analysis", *Proc. Natl., Acad. Sci. USA,* Genetics, vol. 89:5847–5851, (1992).
Velculescu et al., "Serial Analysis of Gene Expression", *Science,* US American Association For The Advancement of Science, vol. 270(20):485–487, (1995).
Klein et al., "Comparative Genomic Hybridization, Loss Of heterozygosity, And DNA Sequence Analysis Of Single Cells", *Proc. Natl. Acad. Sci. USA,* vol. 96(8):4494–4499, (1999).
Klein, Christoph A. et al., "Comparative genomic hybridization, loss of heterozygosity, and DNA sequence analysis of single cells", *Proc. Natl. Acad. Sci. USA,* vol. 96, pp. 4494–4499, (Apr. 1999).
Saiki, Randall K. et al., "Enzymatic Amplification of β–Globin Genomic Sequences and Restriction Site Analysis for Diagnosis of Sickle Cell Anemia", *Science,* vol. 230, pp. 1350–1354, (Dec. 20, 1985).

Nelson, David L. et al., "Alu polymerase chain reaction: A method for rapid isolatin of human–specific sequences from complex DNA sources" *Proc. Natl., Acad. Sci., USA,* vol. 86, pp. 6686–6690, (Sep. 1999).
Hwu, Huey Ru et al., "Insertion and/or deletion of many repeated DNA sequences in human and higher ape evolution", *Proc. Natl. Acad. Sci. USA,* vol. 83, pp. 3875–3879, (Jun. 1986).
Telenius, Hakan et al., "Degenerate Oligonucleotide–Primed PCR: General Amplification of Target DNA by a single Degenerate Primer", *Genomics 13,* ©Academic Press, Inc., (1992).
Kuukasjarvi, Tuula et al., "Optimizing DOP–PCR for Universal Amplification of Small DNA Samples in Comparative Genomic Hybridization", *Genes, Chromosomes & Cancer 18,* © Wiley–Liss, Inc., pp. 94–101, (1997).
Honghua, Li et al., "Amplification and analysis of DNA sequences in single human sperm and diploid cells", *Nature,* vol. 335, pp. 414–417, (Sep. 29, 1988).
Handyside, A.H., et al., "Biopsy of Human Preimplantation Embryos and Sexing by DNA Amplification", *The Lancet,* pp. 347–349, (Feb. 18, 1989).
Cui, Xiangfeng et al. "Single–sperm typing: Determination of genetic distance between the $^G\gamma$–globin and parathyroid hormone loci by using the polymerase chain reaction and allele–specific oligomers", *Proc. Natl. Acad. Sci, USA,* vol. 86, pp. 9389–9393, (Dec. 1989).
Cui, Xiangfeng et al, "Gene–Centromere Linkage Mapping by PCR Analysis of Individual Oocytes", *Genomics 13,* ©Academic Press, Inc., pp. 713–717, (1992).
Zhang, Lin et al., "Whole genome amplification from a single cell: Implications form genetic analysis", *Proc. Natl. Acad. Sci. USA,* vol. 89, pp. 5847–5851, (Jul. 1992).
Lisitsyn, Nikolai et al, "Cloning the Differences Between Two Complex Genomes", *Science* vol. 259, pp. 946–951, (Feb. 12, 1993).
Lucito et al., "Genetic analysis using genomic representations", *PNAS Online,* vol. 95, Issue 8, pp. 4487–4492, (Apr. 14, 1998).

(List continued on next page.)

*Primary Examiner*—Jeffrey Siew
(74) *Attorney, Agent, or Firm*—Foley & Lardner

(57) ABSTRACT

The present invention relates to a novel method for the amplification of DNA, this method being particularly useful for the amplification of the DNA or the whole genome of a single cell, chromosomes or fragments thereof. Described is also the use of the method in DNA analysis for medical, forensic, diagnostic or scientific purposes, like comparative genomic hybridization (CGH)-, fluorescence in situ hybridization (FISH)-, polymerase chain reaction (PCR)-, single strand conformation polymorphism (SSCP)-, DNA sequence-, "loss of heterozygosity" (LOH)-, fingerprint- and/or restriction fragment length polymorphism (RFLP)- analysis.

30 Claims, 17 Drawing Sheets

OTHER PUBLICATIONS

Kallioniemi, Anne et al., "Comparative Genomic Hybridization for Molecular Cytogenetic Analysis of Solid Tumors", *Science,* vol. 258, pp. 818–821, (Oct. 30, 1992).

Speicher, Michael R. et al., "Molucular cytogenetic analysis of formalin–fixed, paraffin–embedded solid tumors by comparative genomic hybridization after universal DNA–amplification", *Human Molecular Genetics,* vol. 2, No. 11, pp. 1907–1914, (1993).

Lee, Henry C., "DNA Typing in Forensic Science", *The American Journal of Forensic Medicine and Pathology 15(4),* ©Raven Press, Ltd., pp. 269–282, (1994).

Du Manoir, Stanis et al., "Quantitative Analysis of Comparative Genomic Hybridization", *Cytometry 19,* © Wiley–Liss, Inc., pp. 27–41, (1995).

Lengauer, Christoph et al., Metaphase and Interphase Cytogenetics with Alu–PCR–amplified Yeast Artificial Chromosome Clones Containing the BCR Gene and the Protooncogenes c–raf–1, c–fms, and c–erb B–2[1], *Cancer Research 52,* pp. 2590–2596, (May 1, 1992).

Stigbrand, T. et al., "Epitope Specificity of 30 monoclonal Antibodies against Cytokeratin Antigens: The ISOBM TD5–1 Workshop", *TumorBiology (19),* pp. 132–152, (1998).

Pantel, Klaus et al. "Frequency and Prognostic significance of isolated tumor cells in bone marrow of patients with non–small–cell lung cancer without overt metastases", *The Lancet,* vol. 347, pp. 649–653, (Mar. 9, 1996).

Forozan, Farahnaz et al., "Genome screening by comparative genomic hybridization", *TIG,* vol. 13, No. 10, © Elsevier Science Ltd., pp. 405–409, (Oct. 1997).

Ried, Thomas et al., "Mapping of Multiple DNA Gains and Losses in Primary Small Cell Lung Carcinomas by Comparative Genomic Hybridization[1]", *Cancer Research 54,* pp. 1801–1806, (Apr. 4, 1994).

Groden, Joanna et al., "Identification and Characterization of the Familial Adenomatous Polyposis Coli Gene", *Cell,* vol. 66, ©Cell Press, pp. 589–600, (Aug. 9, 1991).

Guilford, Parry et al, "E–cadherin germline mutations in familial gastric cancer", *Nature 1(6),* ©Macmillian Publishers, Ltd., pp. 402–405, (1998).

Litt, Michael et al., "Shadow Bands Seen When Typing Polymorphic Dinucleotide Repeats: Some Cases and Cures", *BioFeedback,* vol. 15, No. 2, pp. 280–284, (1993).

Greenblatt, M.S. et al., "Mutations in the p53 Tumor Suppressor Gene: Clues to Cancer Etiology and Molecular Pathogenesis[1]", *Cancer Research 54,* pp. 4855–4878, (Sep. 15, 1994).

Hainaut, P., "IARC Database of P53 gene mutations in human tumors and cell lines: updated ompilation, revised formats and new visualisation tools", *Nucleic Acids Research,* vol. 26, No. 1, ©Oxford University Press, pp. 205–213, (1998).

Bianchi, D.W. et al., "Male fetal progenitor cells persist in material blood for as long as 27 years postpartum", *Proc. Natl. Acad. Sci. USA 93,* pp. 705–708, (Jan. 1996).

Velculescu, Victor E. et al., "Serial Analysis of Gene Expression", *Science,* vol. 270, pp. 484–487, (Oct. 20, 1995).

\* cited by examiner

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agtgggattc cgcatgctag t                                        21

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taactagcat gc                                                  12

DNA AMPLIFICATION OF A SINGLE CELL

CROSS REFERENCE TO RELATED APPLICATIONS

This application is a national phase application of PCT/EP99/06912 filed Sept. 17, 1999, which claims priority to EP 98 11 7745.4 filed Sept. 19, 1998 and EP 98 11 7799.1 filed Sept. 18, 1998, and which are incorporated in their entirety by reference.

BACKGROUND OF THE INVENTION

1. Field of the Invention

The present invention relates to a novel method for the amplification of DNA, this method being particularly useful for the amplification of the DNA or the whole genome of a single cell, chromosomes or fragments thereof. The present invention further relates to the application of the method in DNA analysis for medical, forensic, diagnostic or scientific purposes, like comparative genomic hybridization (CGH), fluorescence in situ hybridization (FISH), polymerase chain reaction (PCR), single strand conformation polymorphism analysis (SSCP), DNA sequence analysis, "loss of heterozygosity" analysis (LOH), fingerprint analysis, and/or restriction fragment length polymorphism analysis (RFLP).

2. Description of the Related Art

Several documents are cited throughout the text of this specification. Each of the documents cited herein (including any manufacturer's specifications, instructions, etc.) are hereby incorporated by reference; however, there is no admission that any document cited is indeed prior art of the present invention.

PCR (polymerase chain reaction) is an extremely powerful in vitro method for the amplification of DNA, which was initially introduced in 1985 (Saiki (1985), Science 230, 1350–1354). By repeated thermal denaturation, primer annealing and polymerase extension, PCR can amplify a single target DNA molecule to easily detectable quantities.

Although PCR was initially applied to amplify a single locus in target DNA, it is increasingly being used to amplify multiple loci simultaneously. Frequently used primers for this general amplification of. DNA are those based on repetitive sequences within the genome, which allow amplification of segments between suitable positioned repeats. Interspersed repetitive sequence PCR (IRS-PCR) has been used to create human chromosome- and region-specific libraries (Nelson (1989), Proc. Nati. Acad. Sci. USA 86, 6686–6690). In humans, the most abundant family of repeats is the Alu family, estimated to comprise 900,000 elements in the haploid genome, thus giving an average spacing of 3–4 kb (Hwu (1986), Proc. Natl. Acad. Sci. USA 83, 3875–3879). However, a major disadvantage of IRS-PCR is that repetitive sequences like Alu or L1 are not uniformly distributed throughout the genome. Alu elements, for example, are preferentially found in the light bands of human chromosomes. Therefore, such a PCR method results in a bias toward these regions while other regions are less represented and thus not amplified or an amplification can only be obtained below detectable levels. Furthermore, this technique is only applicable to those species where abundant repeat families have been identified, whereas other species such as Drosophila and less well characterized animals and plants cannot be subjected to this method.

A more general amplification than with ISR-PCR can be achieved with "degenerate oligonucleotide-primed PCR" (DOP-PCR), with the additional advantage of species independence (Telenius (1992), Genomics 13, 718–725). DOP-PCR is based on the principle of priming from short sequences specified by the 3'-end of partially degenerate oligonucleotides used, during initial low annealing temperature cycles of the PCR protocol. Since these short sequences occur frequently, amplification of target DNA proceeds at multiple loci simultaneously.

DOP-PCR can be applied for generating libraries containing a high level of single-copy sequences, provided pure and a substantial amount of DNA of interest can be obtained, e.g. flow-sorted chromosomes, microdissected chromosome bands or isolated yeast artificial chromosomes (YACs). However, DOP-PCR seems to be not capable of providing a sufficient, uniform amplification of the DNA content of a single cell (Kuukasjärvi (1997), Genes, Chromosomes & Cancer 18, 94–101).

The sensitivity of PCR allows for the analysis of a specific target DNA in a single cell (Li (1988), Nature 335, 414–417). This led to the development of preimplantation genetic disease diagnosis using single cells from early embryos (Handyside (1989), Lancet 1, 347–349) and genetic recombination analysis using a single sperm (Cui (1989), Proc. Nati. Acad. Sci. USA 86, 9389–9393) or oocyte (Cui (1992), Genomics 13, 713–717). However, in all these cases the single cell can be analyzed only once for a given target sequence and independent confirmation of the genotype of any one cell is impossible.

A method called "primer-extension preamplification" (PEP) is directed to circumvent this problem by making multiple copies of the DNA sequences present in a single cell. PEP uses a random mixture of 15-base fully degenerated oligonucleotides as primers, thereby leading to amplification of DNA sequences from randomly distributed sites. It is estimated that about 78% of the genomic sequences in a single human haploid cell can be copied no less than 30 times (Zhang (1992), Proc. Natl. Acad. Sci. USA 89, 5847–5851). However, up to now, a complete and uniform amplification of a whole genome of a single cell has not been documented with methods such as PEP.

A method called representational difference analysis (RDA) is a subtractive DNA hybridization technique that discovers the differences between paired normal and tumor genomes (Lisitsyn (1993), Science 259, 946–951). The minimal amount of DNA needed for RDA shown is 3 ng, corresponding to $\approx 1\times 10^3$ cells. However, only 70% of the genomic sequences can be reproducibly amplified by RDA (Lucito (1998), Proc. Natl. Acad. Sci. USA 95, 4487–4492). Therefore, a uniform and complete amplification of the entire genome of a single cell by representational difference analysis is not possible.

BRIEF SUMMARY OF INVENTION

Therefore, considering the prior art described above, there is a demand for a method capable of substantially uniform and preferably complete amplification of genomic DNA, particularly from a single cell.

Thus, the technical problem consists in providing means and methods which comply with the needs as described above and which eliminate the above-mentioned disadvantages.

The solution to this technical problem is achieved by providing the embodiments characterized in the claims.

Accordingly, the present invention relates to a method for the amplification of DNA, comprising the steps of (a) providing a sample comprising DNA;

(b) digesting the DNA to be amplified with a restriction endonuclease under conditions suitable to obtain DNA fragments of similar length, wherein said restriction endonuclease-is capable of providing 5' overhangs wherein the terminal nucleotide of the overhang is phosphorylated or 3' overhangs wherein the terminal nucleotide of the overhang is hydroxylated on said DNA fragments,
(c) annealing at least one primer to said DNA fragments wherein
  (ca) (caa) simultaneously or subsequently, oligonucleotides representing a first primer are hybridized to said 5' overhangs on said DNA fragments of step (b) and wherein oligonucleotides representing a second primer hybridize to 3' overhangs generated by said first primer and wherein said first and second primer are of different length;
  (cab) said second primer is ligated to said 5' overhangs; and
  (cac) said first primer is removed from said DNA fragments; or
  (cb) (cba) simultaneously or subsequently, oligonucleotides representing a first primer wherein the nucleotide at the 5' terminus is phosphorylated are hybridized to said 5' overhangs on said DNA fragments of step (b) and wherein oligonucleotides representing a second primer hybridize with said first primer; and
  (cbb) said first and second primer are ligated to said DNA fragments; or
  (cc) (cca) oligonucleotides representing said primer are hybridized to said 3' overhangs so that 5' overhangs are generated; and
  (ccb) said primer is ligated to recessed 5' ends of said DNA fragments;
(d) filling in generated 5' overhangs; and
(e) amplifying said DNA fragments with primers which are capable of hybridizing with the complementary strand of said primer(s) of step (c).

As used in accordance with the present invention, the term "DNA fragments of similar length" denotes fragments which, at a statistical level, have a size which is of comparable length. DNA fragments of comparable length are, for example, fragments of 50+/−5 bp or of 4 kbp +/−0.4 kbp. The length range of DNA fragments that is preferably generated is advantageously between about 50 bp and about 4 kbp. DNA fragments of greater or shorter length may be used as well, although they may be amplified or represented to a lesser extent than the above defined fragments. Preferably, the DNA fragments have a size of ≦3 kbp, more preferably said DNA fragments have an average length of about 1000 bp and particularly preferred are fragments of about 200–400 bp.

The term "5' overhangs" as used herein means the 5' phosphate group, provided e.g. by a staggered cleavage of DNA by restriction endonucleases, and denotes a single stranded overhanging 5' end on DNA.

The term "primer" as used herein refers to an oligonucleotide whether occurring naturally as in a purified restriction digest or produced synthetically. The primer is preferably single stranded for a maximum of efficiency in the method of the present invention, and is preferably an oligodeoxyribonucleotide. Purification of said primers is generally envisaged, prior to their use in the method of the present invention. Such purification steps can comprise HPLC (high performance liquid chromatography) or PAGE (polyacrylamide gel-electrophoresis), and are known to the person skilled in the art.

As used herein, the term "restriction endonuclease" refers to bacterial enzymes capable of cutting double stranded DNA at or near a specific nucleotide sequence. The term "filling in" as used herein means a DNA synthesis reaction, initiated at 3' hydroxyl ends, leading to a fill in of the complementary strand. This DNA synthesis reaction is Preferably carried out in presence of dNTPs (dATP, dGTP, dCTP and dTTP). Thermostable DNA polymerases such as Taq polymerases are generally used and are well known to the person skilled in the art.

The term "hybridized to" in accordance with the present invention denotes the pairing of two polynucleotide strands by hydrogen bonding between complementary nucleotides. This hybridization includes hybridization wherein a primer is hybridized directly adjacent to said 5' overhangs as well as hybridization wherein gaps between primers and protruding or receding ends of said DNA fragments are generated. For example, the method of the present invention can be conveniently carried out in the case that a gap is formed between said second primer and the 5' end of the DNA fragment, to name an example, since this gap will be filled in by DNA polymerases, such as Taq polymerases, in embodiments where said Taq polymerase is added before or during annealing and hybridization steps.

Oligonucleotides, representing primers as used in the method of the present invention can be identified, obtained and tested according to the state of the art especially represented by computer based sequence analysis and laboratory manuals, e.g. Sambrook (Molecular Cloning; A Laboratory Manual, $2^{nd}$ Edition, Cold Spring Harbour Laboratory Press, Cold Spring Harbour, N.Y. (1989)).

Furthermore, the setting of conditions for the above described steps of the method of the present invention is well within the skill of the artisan and to be determined according to protocols described, for example in Sambrook et al, loc. cit., or in the appended examples. Further examples of broader range hybridization conditions that can be employed in accordance with the invention are described, inter alia, in Ausubel, "Current Protocols in Molecular Biology", Green Publishing Associates and Wiley Interscience, N.Y. (1989), or Higgins and Hames (Eds) "Nucleic acid hybridization, a practical approach" IRL Press Oxford, Washington DC, (1985).

From the above recited options of the following method for the amplification of DNA is preferred, said method comprising the steps of
(a) providing a sample comprising DNA;
(b) digesting the DNA to be amplified with a restriction endonuclease under conditions suitable to obtain DNA fragments of similar length, wherein said restriction endonuclease is capable of providing 5' overhangs wherein the terminal nucleotide of the overhangs is phosphorylated or 3' overhangs wherein the terminal nucleotide of the overhangs is hydroxylated on said DNA fragments;
(c) annealing at least one primer to said DNA fragments wherein
  (ca) (caa) simultaneously or subsequently, oligonucleotides representing a first primer are hybridized to said 5' overhangs on said DNA fragments of step (b) and wherein oligonucleotides representing a second primer hybridize to 3' overhangs generated by said first primer and wherein said first and second primer are of different length;
  (cab) said second primer is ligated to said 5' overhangs; and
  (cac) said first primer is removed from said DNA fragments;
(d) filling in generated 5' overhangs; and
(e) amplifying said DNA fragments with primers which are capable of hybridizing with the complementary strand of said primer(s) of step (c).

In the case that the two primers are hybridized subsequently, the first primer after hybridization forms a 5' overhang to which the second primer subsequently hybridizes.

The present invention is based on the surprising finding that the combination of the above mentioned steps leads to a substantially uniform and complete amplification of DNA, as demonstrated in Examples 2 and 3. In particular, the method of the invention has been exemplified as follows:

A DNA sample to be amplified can be obtained by isolating a single cell, i.e., for example, a bone marrow stroma cell, a single (tumorous) cell from peripheral blood, a single cell from umbilical vein blood or from a lymph node which is subjected to a digestion with a proteinase. After inactivation of the proteinase-activity, said sample DNA can be digested with a restriction endonuclease with four-nucleotide recognition site, like MseI, leading to DNA fragments of a similar length of about 200 to 400 bp.

The annealing and hybridization of a first and a second primer can be achieved by adding a primer comprising the nucleotide sequence as depicted in SEQ ID NO: 2, and a longer second primer comprising the nucleotide sequence as depicted in SEQ ID NO: 1. Said first primer can be additionally modified in that the last 3' nucleotide of said primer is a dideoxy (dd)-nucleotide. The final concentration of primers in the following ligation reaction was 5 $\mu$M. The ratio between primers used in the present invention to DNA to be amplified was in a range 3 Mio:1, more preferably said ratio was in the range of 300,000:1, most preferably said ration was in the range of 30,000:1. Furthermore, said primers can be pre-hybridized to each other before their addition to said DNA sample.

An annealing reaction was started at a temperature which served also to inactivate said restriction enzyme, i.e. 68° C. Said second primer was ligated to said DNA fragments, in contrast to said first primer which is not ligated since no 5' phosphate necessary for ligation was available. Therefore, the reaction temperature was gradually lowered to a temperature where such a ligation reaction can be carried out, i.e. 15° C. Ligation was obtained by the addition of ATP and a T4-DNA-ligase, to said primers and DNA fragments. After ligation, said first primer was removed from said DNA fragments by a denaturation step, involving a change of temperature to a higher temperature (e.g. of about 68° C.) wherein said primer dissociates from said DNA fragments. Said second primer remained ligated to said DNA fragments.

Resulting 5' phosphate extensions on said DNA fragments were filled in by the addition of DNA polymerases, in the present case Taq and Pwo polymerase, in the presence of dNTPs (dATP, dCTP, dGTP and dTTP), under suitable conditions, as indicated in the examples.

The resulting mixture was then subjected to PCR amplification with said second primer, in a concentration of 1 $\mu$M, as specified in examples 2 and 3.

The amplification product was then further analyzed as described in Example 3.

The method of the present invention is substantially independent from particular precautious measures that have to be observed in methods of the prior art. For example, with the method of the present invention, it is not necessary to extract or purify the DNA of interest (which could lead to losses of DNA) prior to amplification.

Thus, in contrast to the above-mentioned methods for DNA amplification, the method of the present invention can be carried out under amplification conditions which are convenient and optimal for the further use of different adaptor-ligated sequences of choice.

The method of the present invention for the first time allows the amplification of the entire genome of a single cell even from unextracted DNA samples. This enables e.g. the genomic analysis of individual isolated disseminated tumor cells, applying comparative genomic hybridization (CGH) to single cells. Therefore, this method provides, e.g., the means to identify the individual genetic changes in a single cell that might promote dissemination and ectopic growth of disseminated tumor cells with metastatic potential. The genomic profile of such single disseminated cells could provide useful information on whether certain clonal genotypes are associated with disseminative events.

Furthermore, the method of the present invention for the first time allows for the reproducible application of CGH to individual cells, whereas other protocols for "whole genome amplification" such as PEP, DOP-PCR and Alu-PCR do not provide homogenous staining patterns by CGH wherein the origin of test-DNA is a single cell, single chromosomes or parts thereof. This reproducible application of CGH on individual single cells can be explained, inter alia, by the fact that a non-degenerate primer is used that drastically reduces the complexity of primer binding sites of oligonucleotides hitherto used in the DOP and PEP techniques. These previously numerous different sites require equally numerous different specific PCR conditions impossible to achieve during the same reaction. Additionally, since the amplification method of the present invention does not depend on repetitive sequences within the genome (like IRS-PCR), it is possible to reliably amplify the genomic DNA of single cells from species where such repetitive sequences are less frequent or even non-existent.

In a preferred embodiment of the method of the present invention DNA which is amplified is the genome of a single cell or chromosomes or (a) fragment(s) thereof. It has surprisingly been found that the method of the present invention is particularly useful for the analysis of single cells such as disseminating tumor cells, cells obtained from a lymph node, peripheral blood cells, cells from bone marrow aspirates, cells from tumor biopsis, cells obtained from microdissected tissue, or the like. As shown in the appended examples, the method of the present invention is also useful for the analysis of the genome of any single cell (or chromosomes or fragments thereof) wherein said single cell is a rare event containing potentially interesting genetic information. Said single cell which is a rare event might be, inter alia, the cells described hereinabove or embryonic/fetal cells in the venous blood of the mother and the like. The inventive method is particularly useful for the assessment of clonal evolution events of genetic variants in complex (cell) populations, like, inter alia, the clonal evolution of single micro-metastatic cells isolated from peripheral blood, bone marrow, or the like.

The DNA content of a single diploid cell amounts only to 6–7 pg. In prior art DNA amplification methods, like DOP-PCR, at least 25 pg of DNA, corresponding to four diploid cells, are necessary for effective amplification of the entire DNA. However, as demonstrated in Examples 3, 4, 5 and 6 the method of the present invention provides the means to reliably amplify and analyze the entire genome of a single cell.

In another preferred embodiment of the method of the present invention said DNA is present in the form of one copy of a double stranded DNA sequence.

In a further preferred embodiment of the method of the present invention the numerical abundance of said DNA fragments is essentially maintained. As has been found in accordance with the present invention, the method of this invention is capable of reproducibly amplifying genomic sequences. Usually, 80%, preferably more than 90%, more preferably more than 95% and most preferably 99% or more of the genomic sequences can be amplified by the method of the present invention, and the amount of the amplification product for each of those genomic sequences substantially corresponds to their copy number in the genome, as demonstrated in example 4. Therefore, with the method of the present invention it is possible to amplify DNA of a given sample so that the ratio between genomic sequences remain the same before and after said DNA amplification. As discussed above, methods such as RDA (Lucito (1998), PNAS USA 95, 4487–4492) provide for amplifications wherein only 70% of genomic sequences are amplified. It is questionable whether the DNA fragments which are amplified by the prior art methods retain their relative numerical abundance.

In an additional preferred embodiment of the method of the present invention said method comprises, prior to step (a), the step (a') wherein said sample comprising DNA is digested with a proteinase and wherein, after the protein digest in step (b'), the proteinase is inactivated. Preferably, said proteinase is thermo-labil. Accordingly, said proteinase can be thermally inactivated in step (b'). In a preferred embodiment of the method of the present invention the said proteinase is Proteinase K.

In a further preferred embodiment of the method of the present invention said restriction endonuclease does not comprise any cytosine/guanine in its restriction site. It is well known in the art that genomic cytosine and guanine rests can be methylated, which might lead to a reduced enzymatic cut by restriction enzymes.

In a particularly preferred embodiment of the method of the present invention said restriction endonuclease recognizes a motif with four defined bases. Such endonucleases comprise enzymes which have four distinct nucleotides, e.g. MseI, in their recognition side as well as enzymes where an additional wobble base lies within the restriction side, like e.g. ApoI. Preferably, said restriction endonuclease recognizes the consensus sequence TTAA.

In a most preferred embodiment of the method of the present invention said restriction endonuclease is MseI or an isoschizomer thereof. The convenience of using said restriction enzyme is demonstrated in example 2.

The first primer may be longer than the second primer, yet in another preferred embodiment, the present invention relates to the above described method wherein in step (caa) said second primer is longer than said first primer. As demonstrated in the examples, a convenient length difference is 8 to 12 bp.

In another preferred embodiment of the method of the invention the annealing temperature of said second primer in step (caa) is higher than the hybridizing temperature of said first primer to said second primer and said 5' overhangs, as demonstrated in example 2.

In a particularly preferred embodiment of the method of the present invention in step (caa) said first primer comprises 11 or 12 nucleotides and said second primer comprises 21 nucleotides.

It is understood that in accordance with the method of the present invention said first primer in step (caa) or step (cba) is at least partially complementary to said second primer. In a particularly preferred embodiment said first and said second primer comprise a palindromic sequence.

In yet another preferred embodiment of the method of the present invention, the sequence of said first and said second primer is non-degenerate. As described above, other methods known to the person skilled in the art, such as DOP-PCR (Telenias (1992), Genomics 13, 718–725) are based on the use of degenerate oligonucleotides or partially degenerate primers. Such degenerate primers bear a high risk of self-annealing, thereby inhibiting themselves (each other) from binding to target sequences and resulting in the reduction of amplification efficiency.

In a yet more preferred embodiment, said first primer used in step (caa) has the sequence shown in SEQ ID NO: 2 and/or said second primer used in step (caa) has the sequence as shown in SEQ ID NO: 1.

In a further preferred embodiment of the method of the present invention, the last 3' nucleotide of the first primer in step. (caa) of the above described method is modified, such that said primer cannot be elongated by polymerase activity (e.g. Taq polymerase activity). The person skilled in the art is well aware of such modifications and methods for producing such modified oligonucleotides. One of these modifications can be the addition of a dd-nucleotide at the 3' end of the first primer in the above described step (caa).

In an additional preferred embodiment, said first and said second primer of the method of the present invention are hybridized to each other separately from said DNA fragments and are added to said DNA fragments after they hybridized to each other. The addition of the hybridized primers to said DNA fragments is effected prior to step (ca) or step (cb). Such a pre-hybridization of primers leads, inter alia, to a higher hybridization efficiency to said DNA fragments and interfering to chromosomal DNA can be avoided.

In another preferred embodiment of the method of the present invention essentially the whole nuclear genome of a single cell is amplified.

Usually, 80%, preferably more than 90%, more preferably more than 95% and most preferably 99% or more of the whole nuclear genome can be amplified by the method of the present invention.

In a particularly preferred embodiment of the method of the present invention said single cell is a chemically fixed cell. One option for chemically fixing a cell or tissue is formalin. Others are well known to the person skilled in the art.

The inventive method described herein can be applied to DNA of different sources, such as solid tumor DNA isolated from frozen sections and/or cryosections and/or paraffin embedded, formalin fixed specimens. For decades these tissue sections have been stored mainly for histopathological diagnosis. Single cells or small samples, comprising a limited amount of cells, from histopathological tissue can be screened for specific genetic changes and compared with other areas from the same tissue that may exhibit distinctly different histopathological features or, for control purposes, with areas of apparently normal tissue. Global screening of copy number sequence changes within a tumor genome from archival tissue material could increase the knowledge about cytogenetic alterations in solid tumors significantly. A direct comparison of these cytogenetic data with histological and histochemical results and clinical follow up data would become possible.

Furthermore, the method of the present invention may be used for the amplification of single-cell DNA which stems from microdissected and/or laser-microdissected (for example, laser microbeam microdissection preferably combined with laser pressure catapulting) material from, inter alia, cryosections, as shown in the appended examples.

In yet a more preferred embodiment of the method of the present invention steps (a) to (e) are carried out in one reaction vessel. This has the advantage that a potential template loss is avoided and, moreover, an additional opening and closing of the reaction vessel, which may involve contamination and is troublesome, is avoided.

As is evident to the person skilled in the art, the method of the present invention and/or the amplified DNA fragments obtained by the method of the present invention are particularly useful in diagnostic assays and as research tools. Said amplified DNA fragments are, inter alia, useful in areas and fields were only limited amounts of target-DNA is available, such as in forensic investigations (inter alia DNA-fingerprinting), in paleontology and/or in paleoarcheology. Furthermore, the method of the present invention and/or the amplified DNA fragments obtained therewith are particularly useful in preimplantation diagnosis on human and animal embryos. Said method and/or said amplified DNA fragments can furthermore be used, inter alia, in combination with chip-technologies, for identification assays for DNA of contaminating organisms in samples, such as food products or in blood- or liquor samples. Furthermore, the inventive method and/or the amplified DNA fragments obtained by said method may be useful in the detection of contaminating DNA in pharmaceutical compositions or diagnostic solutions.

The present invention therefore further relates to the use of the amplified DNA fragments obtained by the above described method in methods and techniques for DNA analysis. Such methods and techniques are routinely used in prenatal diagnosis, forensic medicine, pathogenic analysis or biological/biochemical research and are known to the person skilled in the art.

In a particularly preferred embodiment of the use of the present invention, the methods for DNA analysis are comparative genomic hybridization (CGH), representational difference analysis (RDA), analytical PCR, restriction enzyme length polymorphism analysis (RFLP), single strand conformation polymorphism analysis (SSCP), DNA sequence analysis, "loss of heterozygosity" analysis (LOH), fingerprint analysis and/or fluorescence in situ hybridization (FISH).

A variety of techniques are now available for genome-wide screening of alterations in copy-number, structure and expression of genes and DNA sequences. These include molecular cytogenetic techniques (such as comparative genomic hybridization (CGH) and multicolor fluorescence in situ hybridization (M-FISH)), as well as molecular genetic techniques (such as representational difference analysis (RDA), differential display, serial analysis of gene expression (SAGE) and microarray techniques). CGH was the first molecular cytogenetic tool that allowed comprehensive analysis of the entire genome (Kallioniemi (1992), Science 258, 818–821). CGH allows for the screening for DNA sequence copy-number changes and provides a map of those chromosomal regions that are gained or lost in a DNA specimen. Because DNA copy-number alterations are of pathogenetic importance in cancer, most of the applications of CGH are in cancer research.

In CGH, which is based on a modified in situ hybridization, differentially labeled test (green) and reference (red) DNAs are co-hybridized to normal metaphase spreads. Copy-number differences between test and reference genomes are seen as green:red fluorescence intensity differences on the metaphase chromosomes. DNA gains and amplifications in the test DNA are seen as chromosomal regions with an increased fluorescence ratio, while losses and deletions result in a reduced ratio. An important contribution of CGH to cancer research has been in pinpointing putative locations of cancer genes, especially at chromosomal sites undergoing DNA amplification. A large number of subregional chromosomal gains and DNA amplifications have been discovered by CGH in some cancers. Because oncogenes and drug-resistance genes are known to be upregulated by DNA amplifications, it has been speculated that DNA amplification sites in cancer could pinpoint locations of novel genes with important roles in cancer progression. Tumor progression implies the gradual transition of a localized, slow growing tumor to an invasive, metastatic and treatment refractory cancer. This progression is thought to be caused by a stepwise accumulation of genetic changes affecting critical genes. By providing genome-scale information of clonal genetic alternations, CGH is extremely useful in the analysis of the biological basis of the tumor progression process. Two cancer specimen taken from the same patient at different stages of progression can be analyzed. For example, genetic changes that are not found in primary tumors, but do occur in their metastases could be informative in pinpointing genetic changes and genes with important roles in the metastatic progression. Metastatic relapse is caused by early dissemination of individual tumor cells, which leave their primary site and enter into the circulation prior to diagnosis and surgical removal of the primary tumor. The vast majority of these cells will be eliminated by the immune system or undergo apoptosis, while others will survive the perils of the circulation, invade tissues at a secondary site, and remain in a dormant stage for years before they finally grow to metastases. This early stage of metastasis formation (minimal residual disease), when tumor cells are few and dispersed, represents the "Achilles' Heel" of cancer, being a promising target for the development of new therapeutic approaches to prevent clinical metastasis. Therefore, in order to screen individual tumor cells by methods like CGH, it is desirable to uniformly and accurately amplify the whole genome of such a cell. Accordingly, the above described method is particularly useful for screening individual tumor cells by CGH and therefore allowing early diagnosis of e.g. neoplastic disorders or patients susceptible to such disorders. The term "neoplastic disorders" is intended to mean the whole spectrum from initiation of malignant transformation in a single cell to advanced cancer disease, including distant solid metastasis.

Based on CGH and DOP-PCR the minimal amount of target DNA so far needed for a reproducible amplification is 50 pg, corresponding to 8 diploid cells (Speicher (1993), Hum. Mol. Genet. 11, 1907–1914). Smaller amounts of genomic DNA could not be reproducibly amplified. Using the method of the present invention a further reduction of the amount of DNA necessary for a single test is possible.

The method of the present invention not only provides for example uniformly amplified DNA for the subsequent use in CGH, but also allows the reliable uniform amplification of even smallest quantities of DNA for further techniques and methods, wherein samples contain only small amounts of DNA. For example, in forensic science, DNA typing procedures have become increasingly important in the last few years (Lee (1994), Am. J. Forensic Med. Pathol. 15, 269–282): PCR and RFLP analysis, also called fingerprint analysis, are carried out with only minute available quantities of DNA found in sperm, blood traces or individual cells and the like.

Another important application of the presented method is prenatal diagnosis using embryonic or fetal cells in maternal blood. The ability to use embryonic or fetal cells enriched from maternal blood of pregnant women for prenatal diagnosis of chromosomal abnormalities has been a long-sought goal for those pursuing a non-invasive alternative to current methods, such as amniocentesis or chorionic villus sampling. The localization and identification of novel disease genes allows for mutation analysis or linkage studies on fetuses at risk for single gene disorders or chromosomal abnormality etc. The method of the present invention improves the accuracy as well as applicability of methods for the diagnosis of preimplantation genetic disorders or for the diagnosis on fetal cells isolated from maternal blood, whereby analyses can be performed on a single cell level, thus abolishing the need for preceding enrichment of cells. As demonstrated in the appended examples, the method of the present invention provides for the reliable amplification of DNA from a single fetal or embryonic cell isolated from maternal blood, inter alia, from the umbilical vein blood.

The present invention further relates to a kit comprising at least one primer and/or a first and/or a second primer as defined above. Advantageously, the kit of the present invention further comprises, besides said primer and/or the primers, optionally, proteinases, restriction enzymes, DNA-ligases (such as T4-DNA-Ligase), DNA-polymerases (such as Taq polymerase), Pwo polymerase, and/or ThermoSequenase, as well as (a) reaction buffer(s) and/or storage solution(s). Furthermore, parts of the kit of the invention can be packaged individually in vials or in combination in containers or multicontainer units. As it has been usefully demonstrated in the examples, a Proteinase K-digestion, a four-cutting restriction-endonuclease and primer(s) as defined above are suitable for the method of the invention. Thus, the kit of the invention preferably comprises Proteinase K, a four-cutting restriction endonuclease (such as MseI), Taq and/or Pwo polymerase, primer(s) as defined above, and/or T4-Ligase. The kit of the present invention may be advantageously used for carrying out the method of the invention and could be, inter alia, employed in a variety of applications referred to above, e.g. in diagnostic kits or as research tools. Additionally, the kit of the invention may contain means for detection suitable for scientific and/or diagnostic purposes. The manufacture of the kits follows preferably standard procedures which are known to the person skilled in the art.

Furthermore, the present invention relates to the use of a first and/or second primer as defined above for the preparation of a kit for carrying out the method of the present invention.

Throughout this specification and the claims which follow, unless the context requires otherwise, the word "comprise", and variations such as "comprising" and "comprising", will be understood to imply the inclusion of a stated integer or step or group of integers or steps but not the exclusion of any other integer or step or group of integer or step.

(B) Sequence of the mutation found in codon 215. The single control cells contained the wild type sequence with an A at nt 643 (upper two sequences), whereas the tumor cells were mutated at this position showing a A→G mutation (lower two sequences). The sequences of four of the eight cells are shown.

Figure 7:
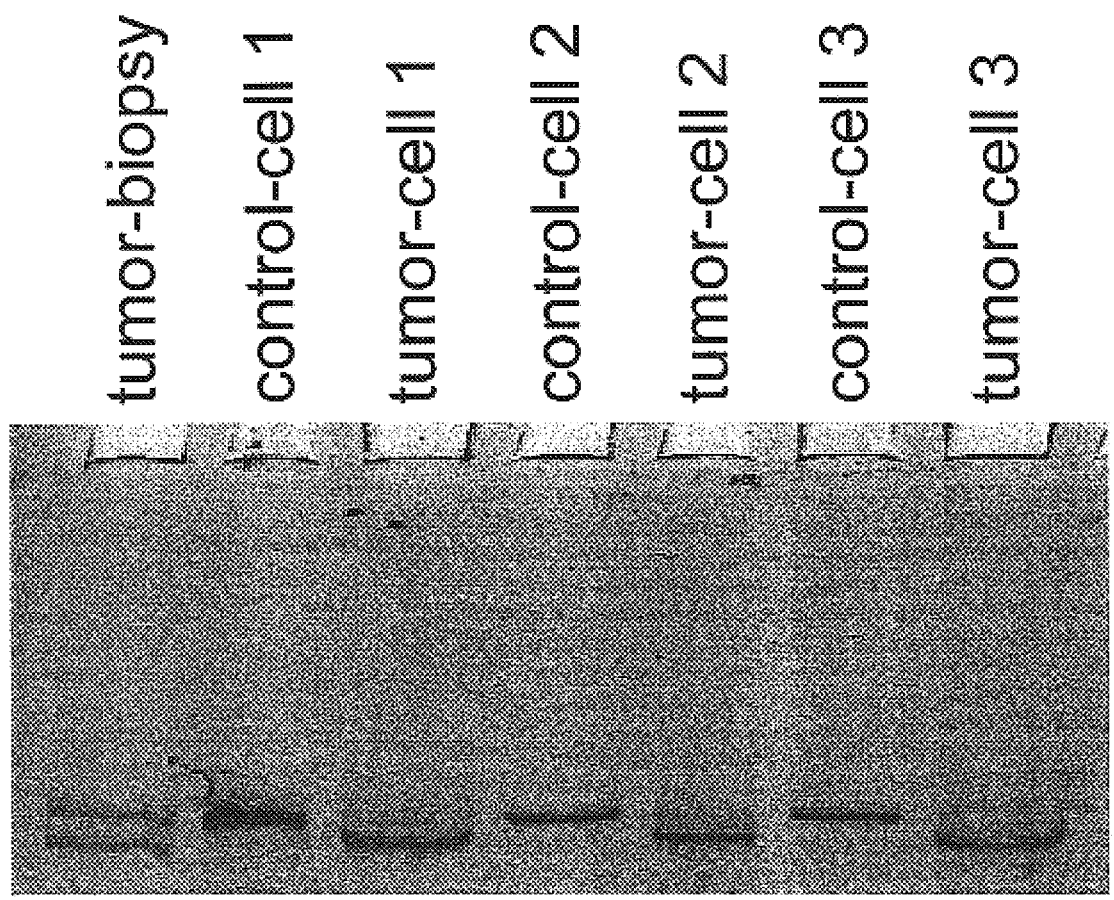

FIG. 7. SSCP analysis of exon 6 of the tumor suppressor gene p53. Three normal cells and three tumor cells as well as a biopsy from a metastasis were subjected to SSCP analysis. The PCR products of the single normal cells migrate at different position than those of the tumor cells. The point mutation is easily in all tumor cells. Interestingly, both bands can be seen in the biopsy sample that obviously contained normal stromal or infiltrating cells in addition to tumor cells.

Figure 8:
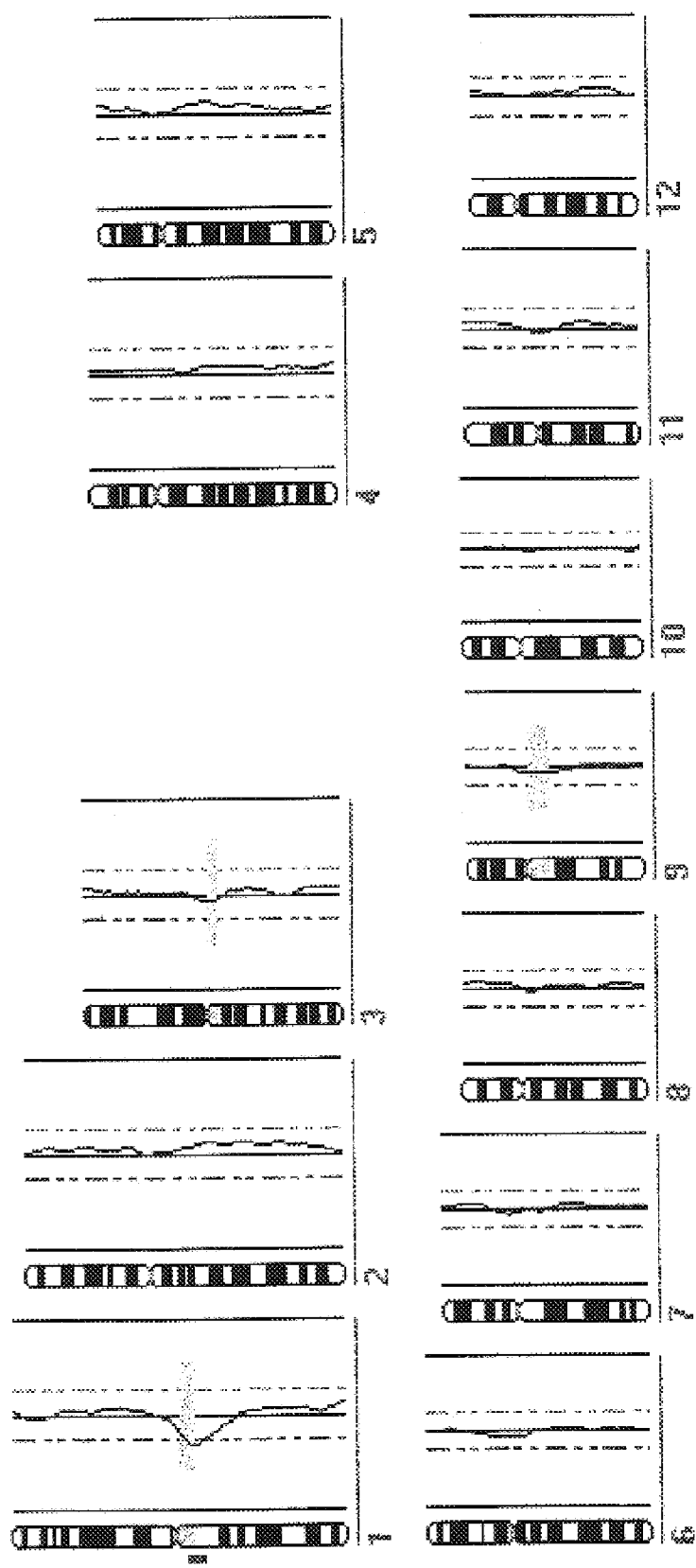
Figure 8:
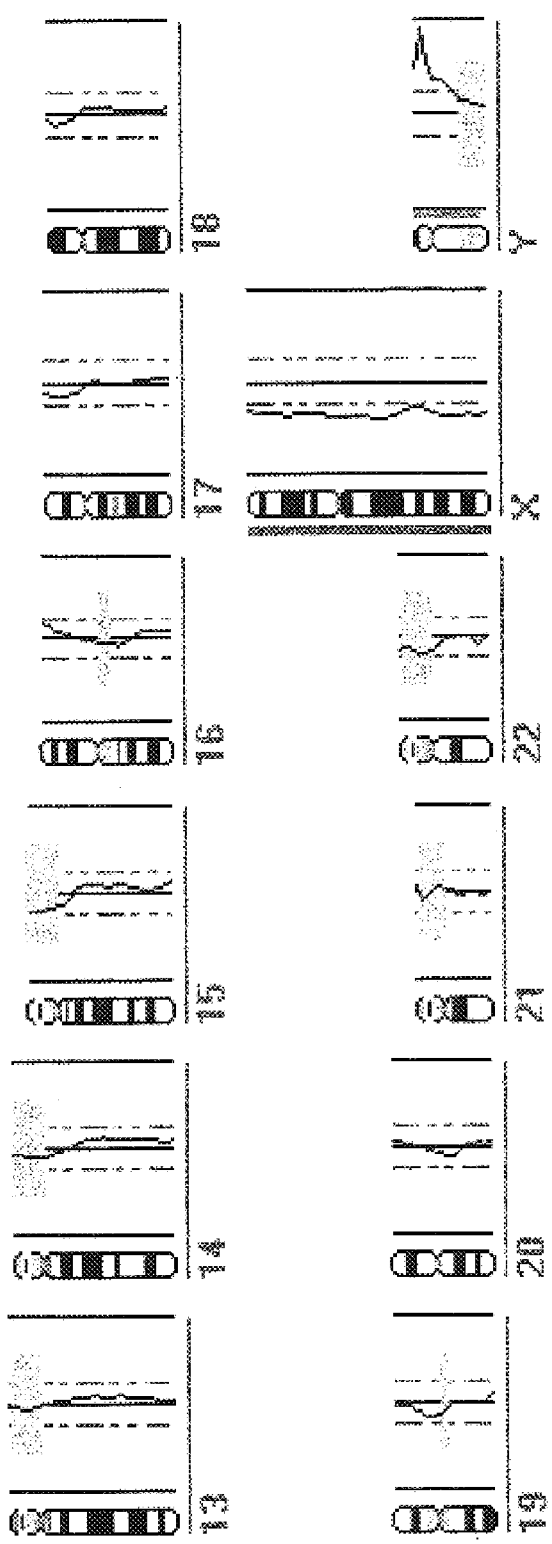

FIG. 8. CGH profile of a single leukocyte isolated from the umbilical cord of a newborn boy. The cell was stained using an antibody directed against fetal hemoglobin, a marker frequently used to detect cells from the child in the peripheral blood of the mother during pregnancy. Female DNA served as control DNA in the CGH experiment. The quality of the hybridization can then be assessed by the demonstration of a "loss" of the X chromosome and a "gain" of the Y chromosome as a consequence of this experimental design. As it is depicted, the sex could be successfully determined as well as all autosomes showed normal profiles.

Figure 9:
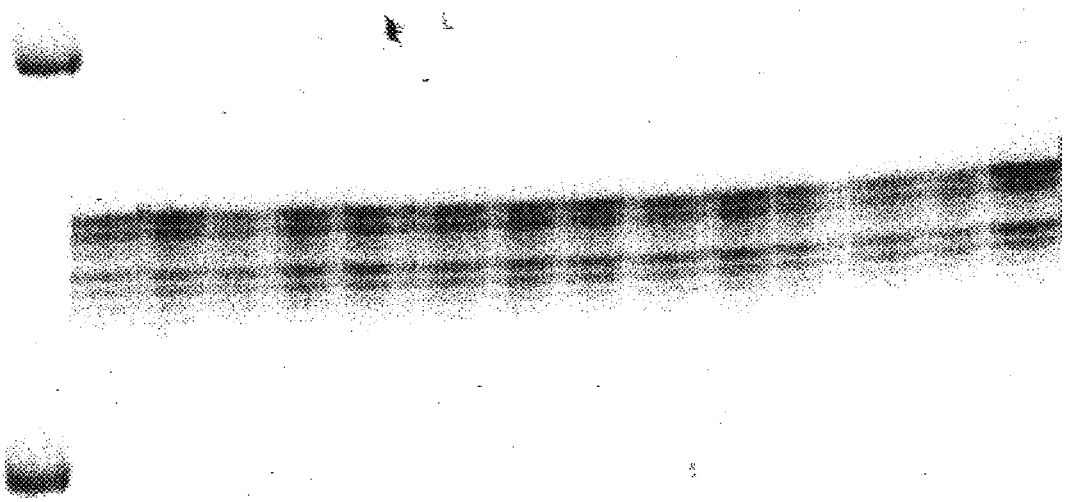
Figure 10A:
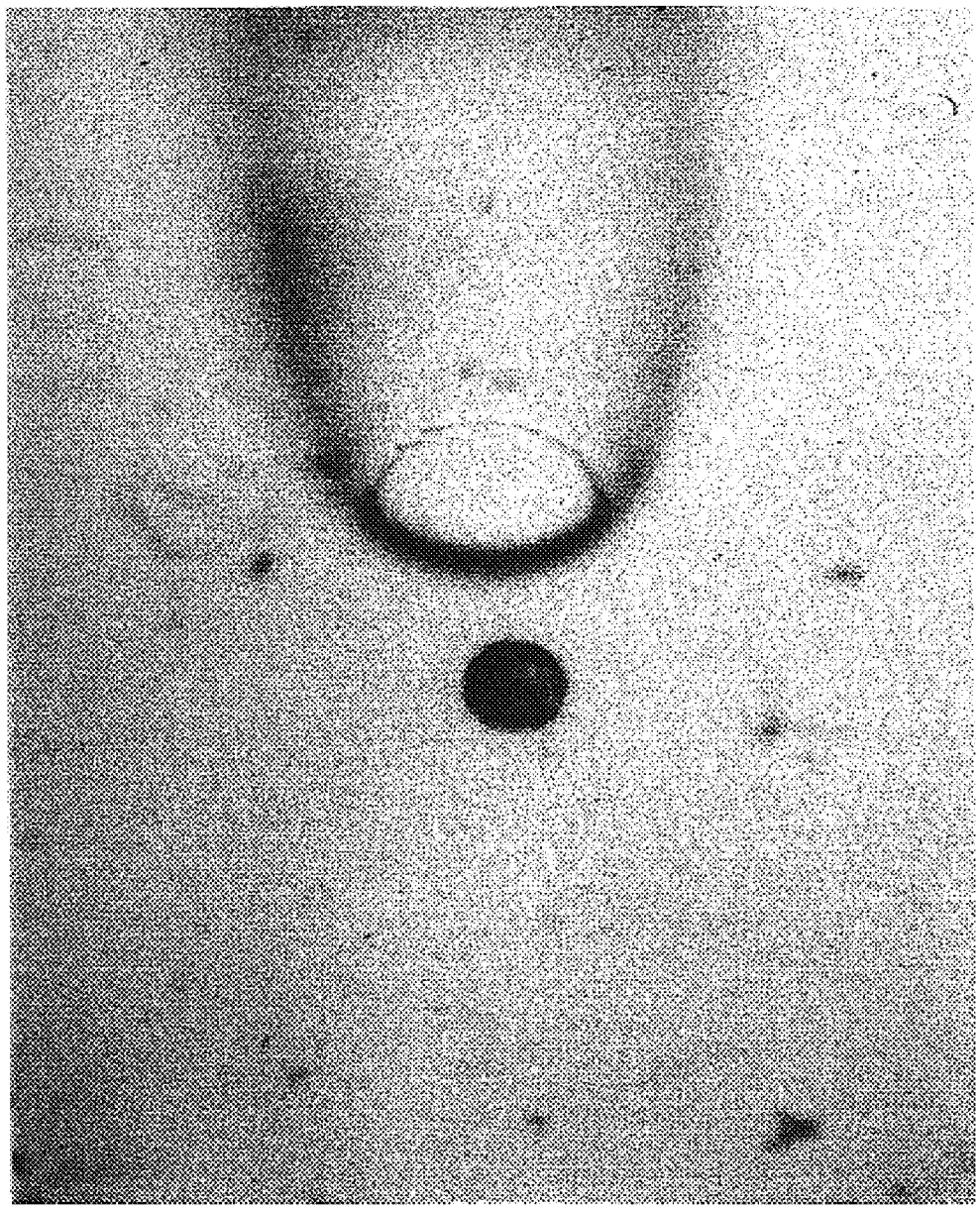
Figure 10B:
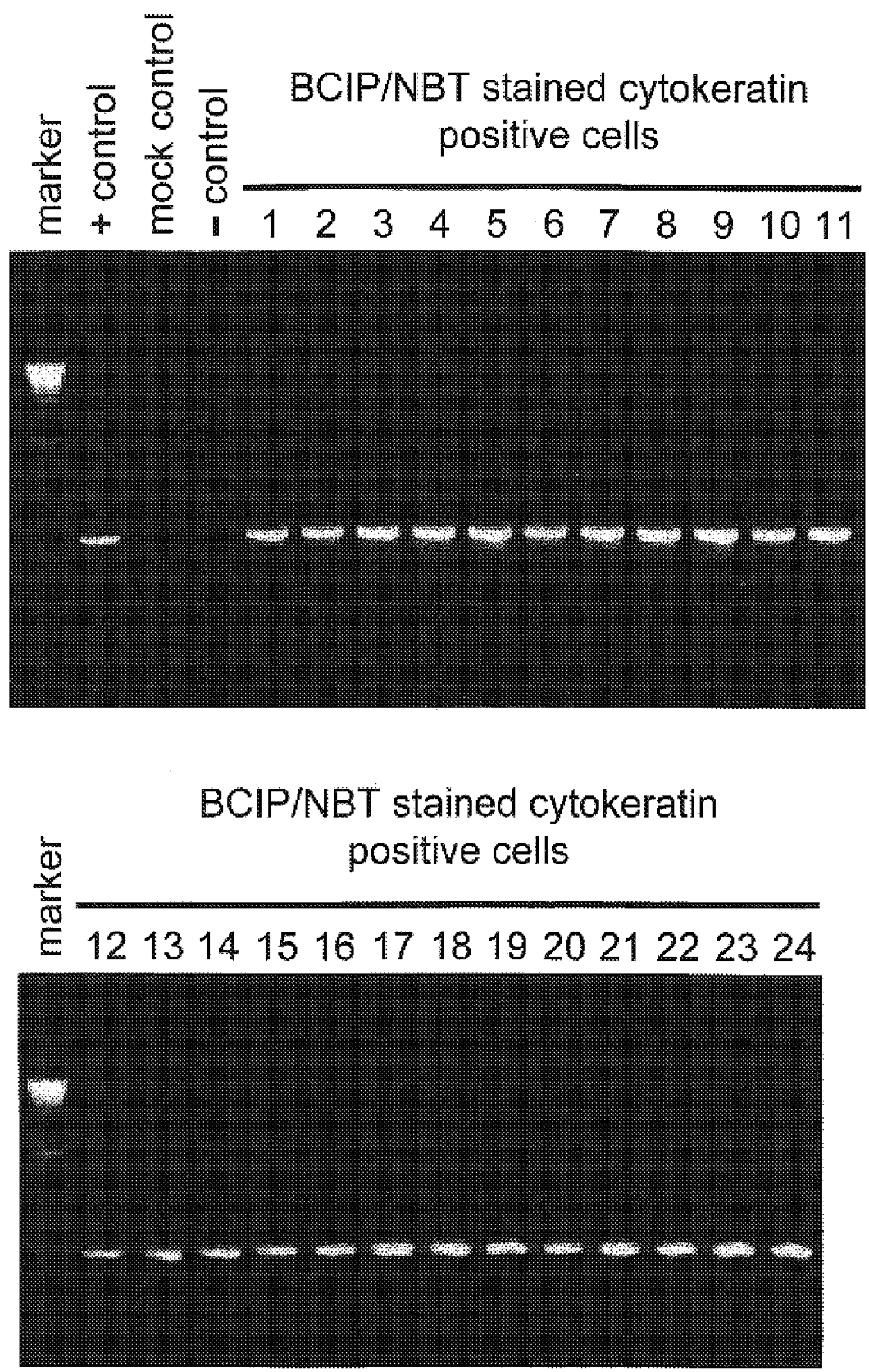
Figure 10C:
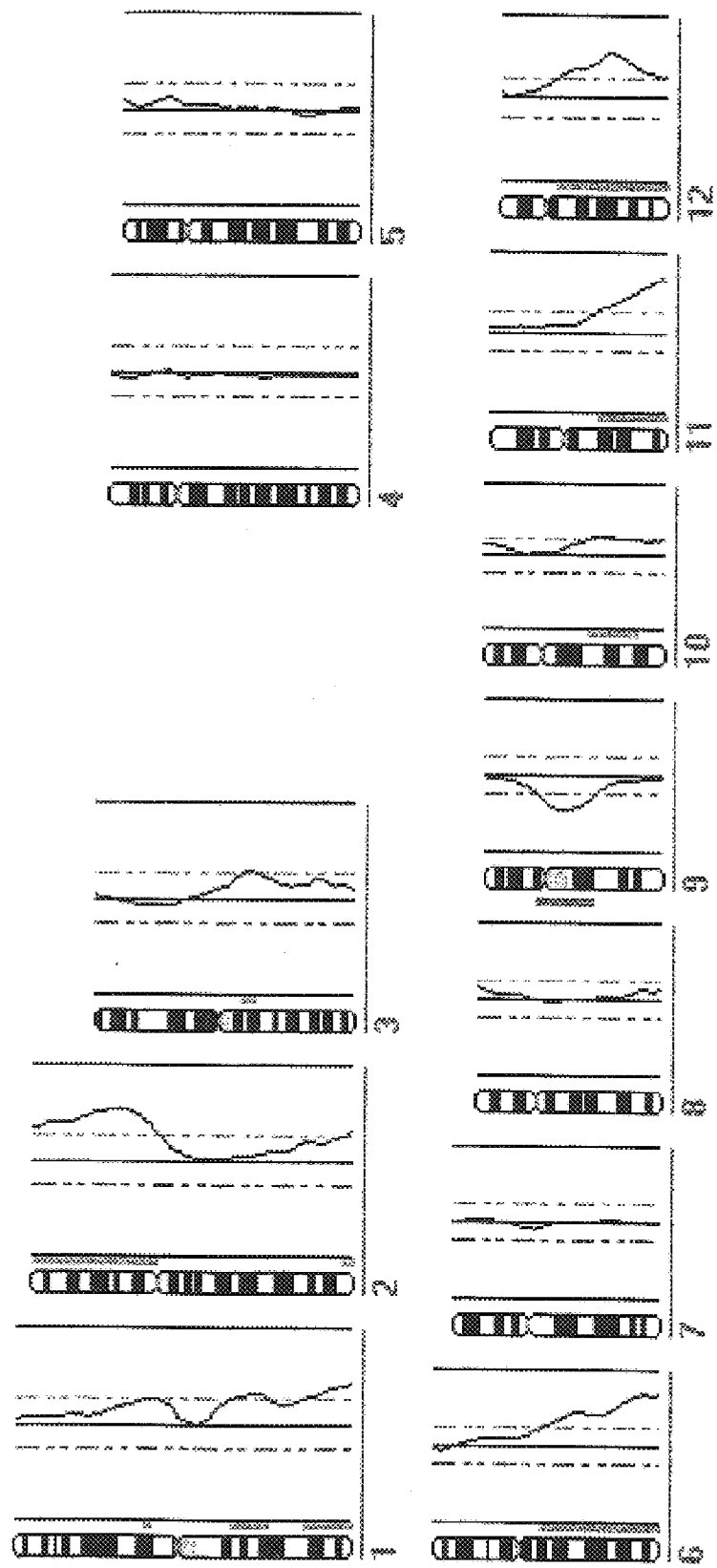
Figure 10C:
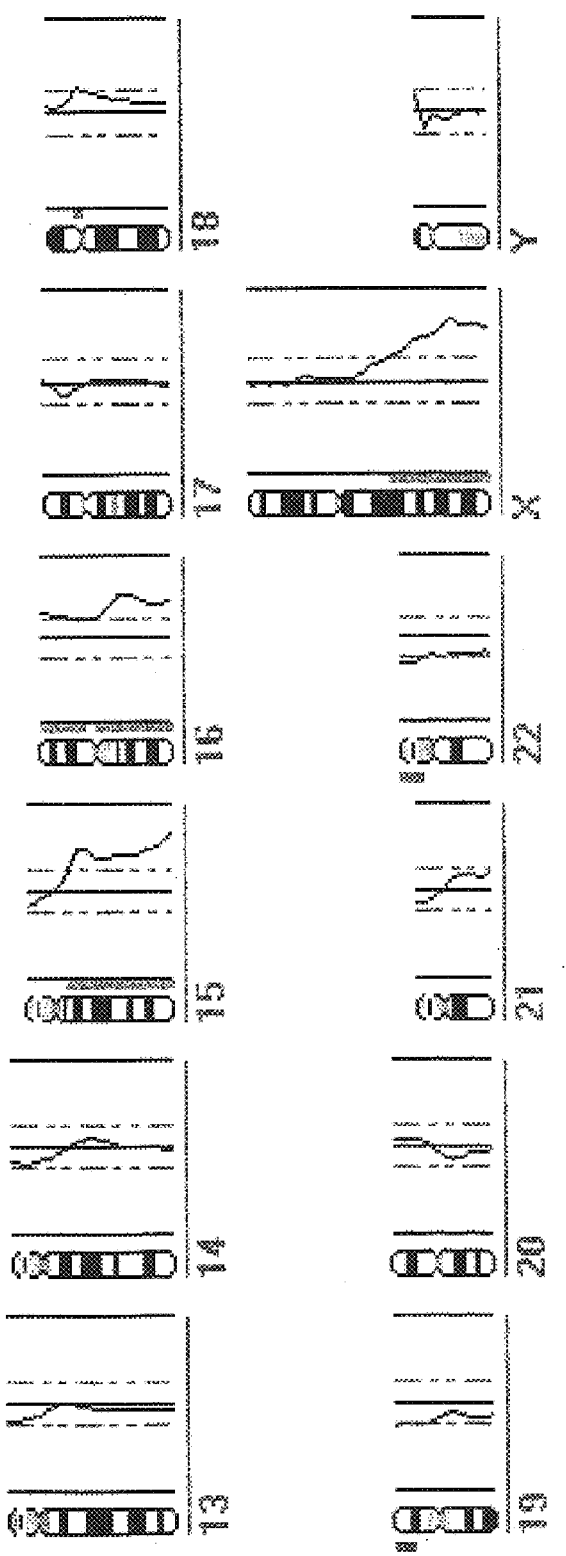

FIG. 9. Identification of polymorphisms in single cells for fingerprint analysis. In microsatellite PCR the size of a band corresponds to a polymorphism. The identification of a polymorphism requires therefore that the size is not changed by the procedure. Here, PCR products of a dinucleotide microsatellite marker (D5S1975) derived from 12 single cells are shown next to the bands generated from the DNA of thousands of cells (+). The two alleles of the marker amplified from the individual cells and the positive control migrate at the same size. No loss of heterozygosity is observed.

FIG. 10. (A): Isolation of a BCIP/NBT stained cell using alkaline phosphatase by micromanipulation. (B): PCR analysis of the genomic sequence of cytokeratin 19 (CK19) of 24 consecutively isolated cells that were immuncytochemically stained with the mab A45 B/B3, as mentioned in example 15. No loss in sensitivity as compared to immunofluorescent labeling is observed, the whole genome amplification, exemplified by the CK19 PCR, was successful in all cells. C: CGH profile of cell number 4 from FIG. 10B. A variety of aberrations are present in the genome.

DETAILED DESCRIPTION OF THE INVENTION

The invention will now be described by reference to the following biological examples which are merely illustrative and are not to be construed as a limitation of scope of the present invention.

EXAMPLE 1

Digestion of DNA

In a comparative study several restriction enzymes recognizing a four base motif were tested whether they are able to generate DNA fragments from 0.2–2 kb length that are suitable for the method of the invention. Fragments with an average length of 256 bp ($4^4$) were predicted under the premise that the four bases are evenly distributed and that the digest is complete. Five enzymes were tested: TaqI (TCGA), Csp6I (GTAC), MspI (CCGG), AciI (CCGC, GCGG) and MseI (TTAA). Only MseI, an enzyme without a C/G in its recognition site, produced a smear visible in the range from 100–1500 bp length and was therefore used in the protocol.

EXAMPLE 2

Amplification of DNA of a Single Cell

In order to avoid template loss, all preparatory steps were performed in one tube. For DNA isolation, restriction enzyme digest, primer ligation and PCR-amplification all buffers and conditions were adjusted for optimal performance to guarantee highest reliability and reproducibility. Generally, high concentrations of proteinase K, MseI, T4 DNA ligase and Taq polymerase gave the best results.

A single cell (e.g. peripheral blood lymphocyte or bone marrow stoma cell) in 1 $\mu$l pick buffer (50 mM Tris/HCl, pH 8.3, 75 mM KCl 3mM $MgCl_2$, 137 mM NaCl) was added to 2 $\mu$l Proteinase K digestion buffer (10 mM Tris-Acetate (pH 7.5), 10 mM Mg-Acetate, 50 mM K-Acetate (0.2 $\mu$l of Pharmacia One-Phor-AII-Buffer-Plus), 0.67% TWEEN (Sigma), 0.67% Igepal (Sigma), 0.67 mg/ml Proteinase K) and incubated for 10h at 42° C. in a PCR machine with heated lid. Proteinase K was inactivated at 80° C. for 10 minutes. After inactivation of Proteinase K, Mse I restriction endonuclease digest was performed in 5 $\mu$l by adding 0.2 $\mu$l One-Phor-AII-Buffer-Plus, 0.5 $\mu$l Mse I (10 U; New England Biolabs) and 1.3 $\mu$l $H_2O$, for 3 hours at 37° C. Annealing of primers was achieved by adding MseLig 21 primer, as shown in SEQ ID: 1, (5'-AGT GGG ATT CCG CAT GCT AGT-3') and MseLig 12 primer, as shown in SEQ ID: 2, (5'-TAA CTA GCA TGC-3', 0.5 $\mu$l each of 100 $\mu$M stock solution, Metabion), 0.5 $\mu$l One-Phor-AII-Buffer and 1.5 $\mu$l $H_2O$, giving a final concentration of the primers in the PCR reaction of 1 $\mu$M. Annealing was started at temperature of 65° C. (also serving to inactivate the restriction enzyme before ligation) and was shifted down to 15° C. with a ramp of 1° C./minute. At 15° C. 1 $\mu$l ATP (10 mM) and 1 $\mu$l T4-DNA-Ligase (5 U; Boehringer Mannheim) was added and primers and DNA fragments were ligated over night.

For primary PCR amplification 40 $\mu$l consisting of 3 $\mu$l PCR buffer (Boehringer Mannheim, Expand Long Template, buffer 1), 2 $\mu$l dNTPs (10 mM) and 35 $\mu$l $H_2O$ were added to the 10 $\mu$l reaction volume. The PCR-program started with a denaturation step at 68° C. for 4 minutes to remove the MseLig-12 oligonucleotide, addition of 1 $\mu$l (3.5 U) of DNA polymerase mixture of Taq and Pwo polymerase (Boehringer Mannheim, Expand Long Template) and 3 minutes incubation for the fill-in-reaction. The Stratagene Robocycler was programmed to 94° C. (40 sec.), 57° C. (30 sec.), 68° C. (1 min. 15 sec.) for 14 cycles; 94° C. (40 sec.), 57° C. (30 sec.), 68° C. (1 min. 45 sec.) for 34 cycles; and 94° C. (40 sec.), 57° C. (30 sec.), 68° C. (5 min) for the final cycle.

As to the choice of primers, HPLC purification and a high concentration in the annealing/ligation reaction (5 $\mu$M) were prerequisites for successful performance. Under these conditions amplification of the digested single cell DNA resulted in a smear of a size similar to a complete digest of 1 pg high molecular weight DNA.

EXAMPLE 3

CGH With Amplified DNA From Peripheral Blood Lymphocytes

DNA isolated from a single unfixed and paraformaldehyde (PFA)-fixed peripheral blood lymphocyte was amplified as described in Example 2 and competitively hybridized with 1 $\mu$g nick-translated, unamplified placenta DNA. Labeling was most efficient using ThermoSequenase in combination with a ratio of dTTP/bio-dUTP of 7/1. Reamplification was performed in 30 $\mu$l using 0.5 $\mu$l LigMse-21 primer (100 $\mu$M), 1 $\mu$l dNTP (dATP, dCTP, dGTP, 10 mM each, 8.6 mM dTTP) and 1.3 $\mu$l biotin-16-dUTP (1 mM, Bboehringer Mannheim), 13 U ThermoSequenase (USB) in 1×ThermoSequenase buffer and 0.5 $\mu$l of the primary PCR. In total 25 cycles were programmed with the temperatures set to 94° C. (1 min.), 65° C. (30 sec.), 72° C. (2 min.) for 1 cycle; 94° C. (40 sec.), 65° C. (30 sec.), 72° C. (1 min. 30 sec.) for 94° C. (40 sec.), 65° C. (30 sec.), 72° C. (2 min.) for 9 cycles and an additional final extension step at 72° C. for 5 min. Before using 2 $\mu$g reamplified, labeled DNA, primers were removed by MseI digest. Nick translation of control DNA, as well as MCF-7 cell line DNA, metaphase spread preparation and hybridization was done as published in Speicher (1993), *Hum. Mol. Genet* 2, 1907–14. Images were captured with the Leica DMXA-RF8 microscope, equipped with a Sensys CCD camera (Photometrix, Tucson, Ariz.). Quantitative evaluation of the ratio of test and control DNA was done according to du Manoir (1995), *Cytometry* 19, 27–41, using the Leica software package Q-CGH. Seven to twelve metaphase spreads fitting the requirements of the program were evaluated in each experiment. In the course of experiments the profiles became smoother with no change in results when PCR-amplified and labeled control DNA was used instead of nick-translated chromosomes (compare FIG. 1: PCR-labeled control DNA, and FIG. 2: 0.5 µg nick-translated control DNA). 0.5 µg control DNA was modified and amplified as described for single cells and labeled in the reamplification reaction with digoxigenin-UTP (Boehringer Mannheim). The smoother CGH profiles probably reflect that fragment size and blocking efficacy for repetitive sequences are identical under these conditions for the two DNA samples.

In seven independent single cell experiments the obtained CGH profiles, CGH was carried out as described in Speicher (1993), Hum. Mol. Gen. 2, 1907–1914) showed no PCR-related chromosomal gains or losses detectable as a significant deviation from the central line. In fact, in all cases analyzed the sex of donor could be confirmed. PFA fixation had no effect on the outcome of the experiment.

EXAMPLE 4

Detection of Chromosomal Changes in a Patient With Down's Syndrome

Figure 1:
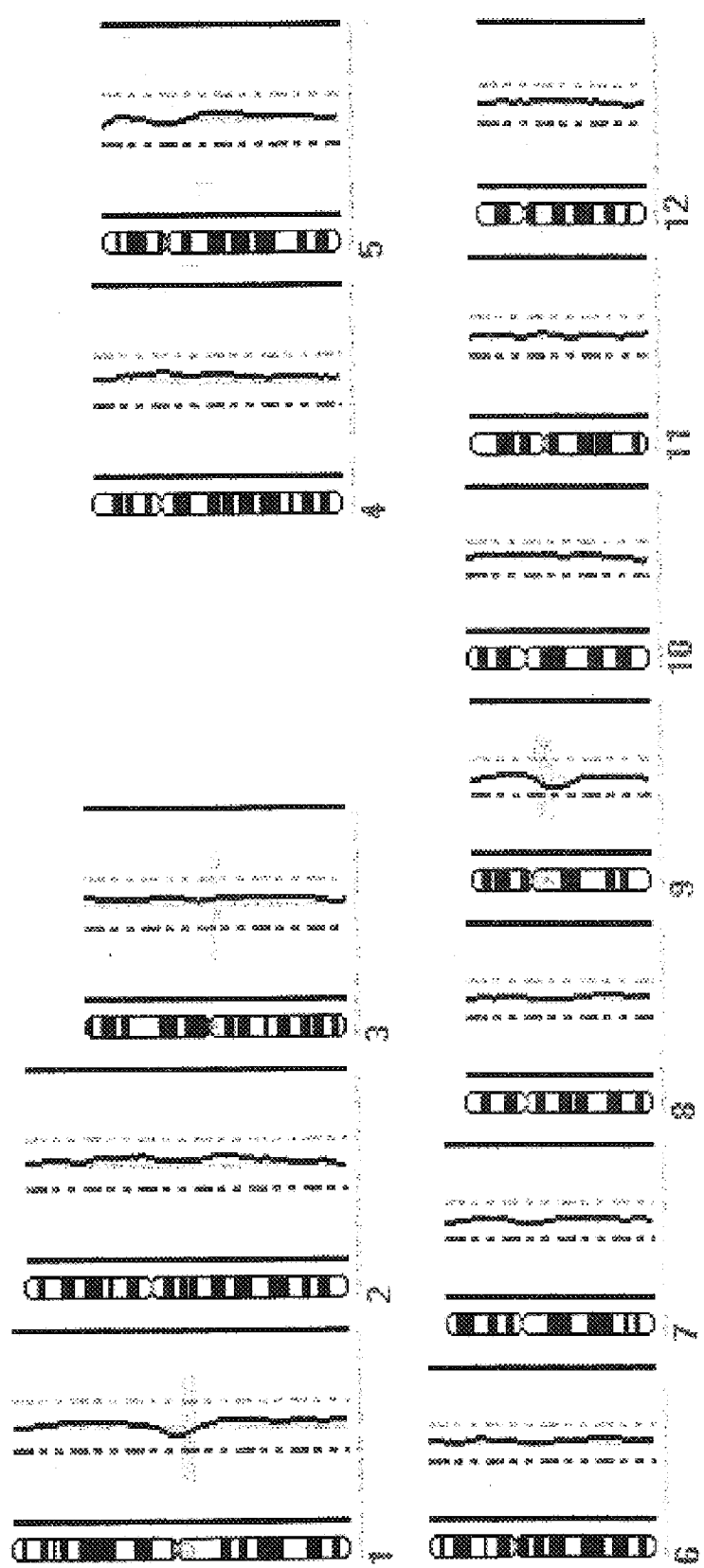
FIG. 1. CGH-profile of a peripheral blood leukocyte of a patient with Down's syndrome. In order to be considered significant, deviations from the black midline have to cross the right (chromosomal gain) or left (chromosomal loss) punctate line. The black horizontal bars indicate regions excluded from analysis due to the prevalence of heterochromatic DNA. The chromosome 21 (except for the blocked heterochromatic region) was found to be amplified entirely, whereas all other chromosomes showed normal profiles. Deviations from the midline have to cross the right (chromosomal gain) or left (chromosomal loss).
Figure 1:
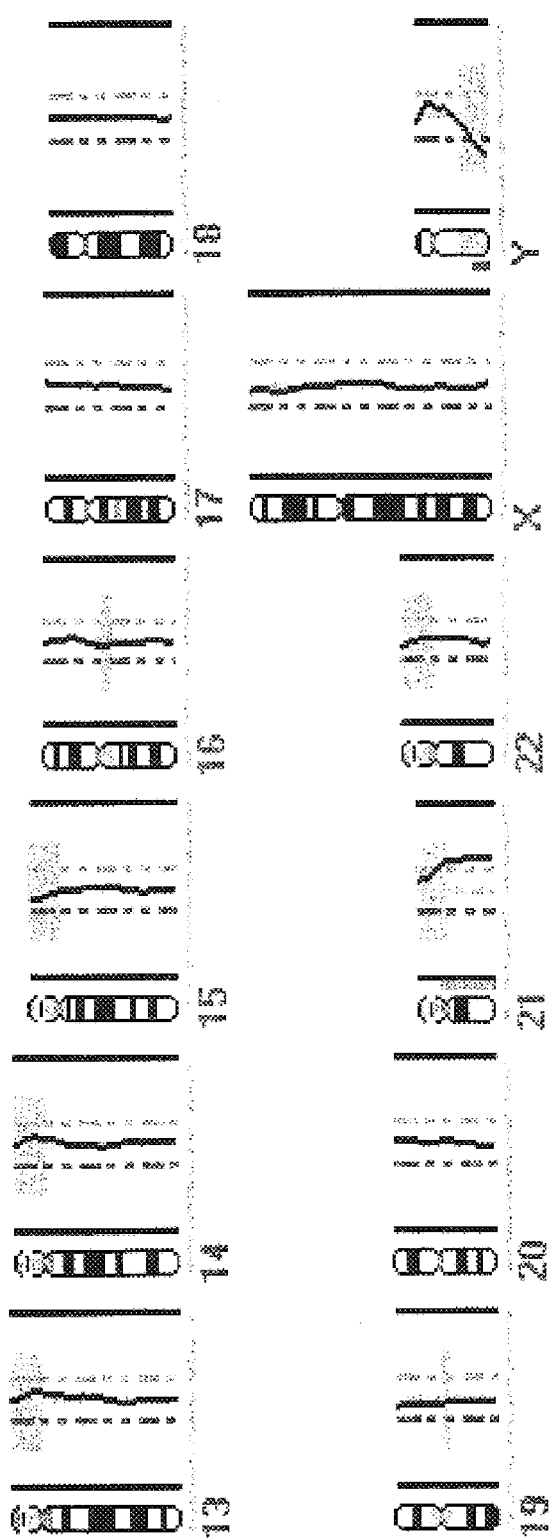

In order to determine whether known chromosomal changes could be detected by the single cell analysis, DNA of a single leukocyte from a blood sample of a patient with Down's syndrome and its DNA was isolated and amplified as described in Example 2. The CGH-profile showed a gain of chromosome 21 as single detectable abnormality (FIG. 1).

EXAMPLE 5

Detection of Chromosomal Alterations in Single MCF-7 Cells

Figure 2:
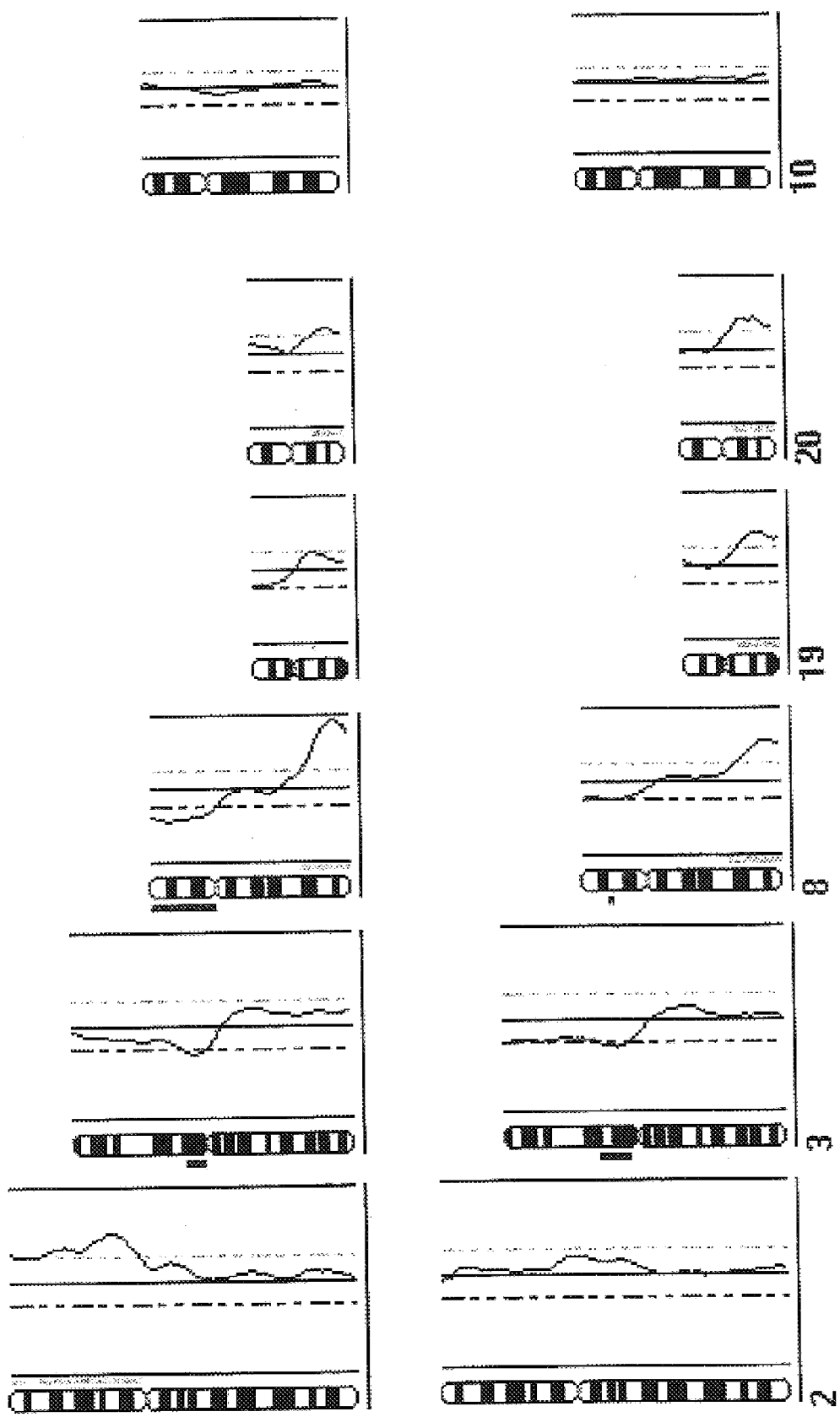
FIG. 2. Comparison of the CGH profiles of a conventional CGH experiment using 1 µg nick-translated DNA prepared from the MCF-7 cell line and from a single cell of the same cell line after PCR-amplification. For both experiments chromosomes 2, 3, 8, 19 and 20 are shown for comparison of differences between the single cell and the cell line. The single cell profiles are depicted in the upper panel, the cell line profiles in the lower. Bars on the right side of the chromosome symbol indicate chromosomal gains, bars on the left side chromosomal losses of the test-DNA. Chromosome 10 represents one example, where no change could be seen in either sample. Deviations from the midline have to cross the right (chromosomal gain) or left (chromosomal loss).
Figure 3:
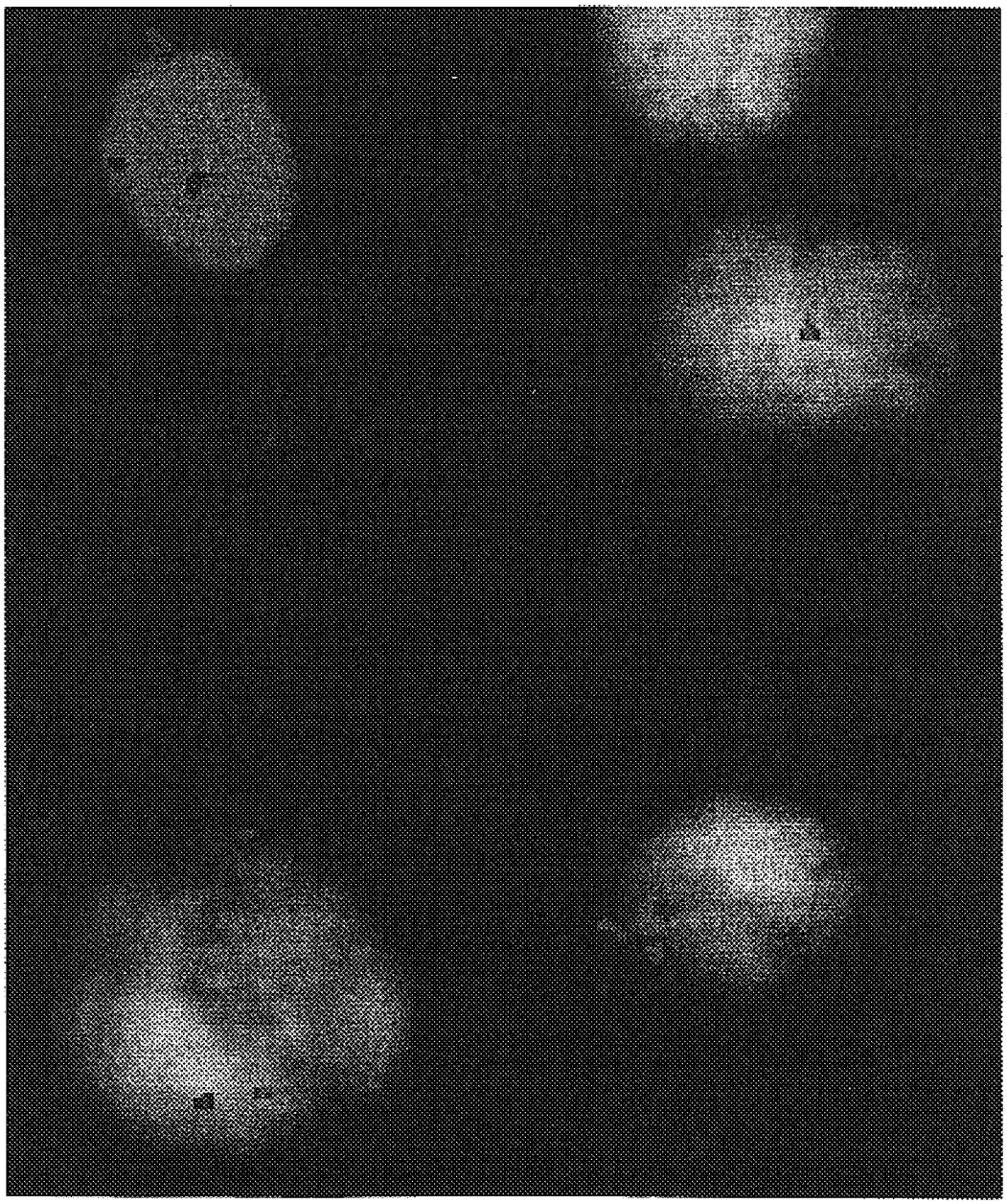
FIG. 3. Two-color interphase-FISH on MCF-7 cells with YAC clones for 2p25 (red) and 2q31 (green). In the upper right cell three signals can be identified for the 2p region but only two for 2q. The other cells show two signals for both the 2p and 2q probe.

Detection of more complex numerical alterations was verified by comparing the ratio profiles of a single cell from the MCF-7 breast cancer cell line (ATCC HTB-22) and of 1 µg unamplified DNA isolated directly from MCF-7 cells (FIG. 2 and Table 1). The extra gain on chromosome 2p as detected in single cell CGH was not due to a PCR artefact but was also seen by two-color interphase FISH (FISH analysis was performed as described in Lengauer [(1992), Cancer Res. 52, 2590–6] performed with the CEPH-YACs 695h7 and 963d11 probes, mapped to 2p25 and 2q31, respectively). As summarized in Table 2, 16% of all cells evaluated showed 3 signals for 2p but only two for 2q (FIG. 3). A numerical abnormality present in only 16% of a cells population does not change a CGH-profile made of pooled DNA (du Manoir (1995), loc. cit.), however, it may become clearly visible if CGH is performed with a single cell from this minor subclone.

TABLE 1

Comparison of changes found in MCF-7 and a single cell of the same cell line. Most of the changes found in MCF-7 can be detected in a single cell. Differing changes of either the cell line or the single cell are shown in bold letters.

| Hybridization with | chromosomal gains | chromosomal losses |
|---|---|---|
| Cell line DNA | 8 q, 11 p, 11 q, 15 q, 19 q, 20 q | 3 p, 8 p |
| Single cell amplified DNA | 2 p, 8 q, 11 p, 15 q, 19 q, 20 q | 3 p, 8 p |

TABLE 2

Results of interphase cytogenetics on cells from the breast cancer cell line MCF-7 and normal lymphocytes. 100 nuclei were evaluated in each case.

|  | 1 × 2 p 1 × 2 q | 1 × 2 p 2 × 2 q | 2 × 2 p 1 × 2 q | 2 × 2 p 2 × 2 q | 2 × 2 p 3 × 2 q | 3 × 2 p 2 × 2 q | 3 × 2 p 3 × 2 q | 4 × 2 p 2 × 2 q | 4 × 2 p 3 × 2 q |
|---|---|---|---|---|---|---|---|---|---|
| MCF-7 | 6 | 0 | 2 | 70 | 0 | 16 | 3 | 2 | 1 |
| normal cell | 1 | 3 | 4 | 89 | 1 | 1 | 1 | 0 | 0 |

EXAMPLE 6

CGH Analysis of a Single Tumor Cell From a Patient With a Primary Breast Cancer

The extremely rare individual tumor cells in bone marrow were identified in marrow aspirates by indirect immunofluorescence with the monoclonal cytokeratin antibody A45 B/B3 (Micromet). Cytokeratin-epitopes recognized by A45B/B3 have been mapped to cytokeratins 8, 18 and heterodimers of 8/18 and 8/19 (Stigbrand (1998), Tumor Biol. 19, 132–52).

Aspiration of the bone marrow samples and isolation of mononucleated cells was performed as described (Pantel (1996), Lancet 347, 649–653). Cells were washed in PBS and fixed for 5 minutes in 0.2% PFA. Blocking of unspecific binding with 5% AB-serum as well as incubation with 10 µg/ml A45-B/3 (Micromet) in 2% Pepton/PBS, 10 minutes each, was performed in the presence of 0.05% saponin (Sigma) to permeabilize the cells. After washing the cells in 2% Pepton/PBS, the antigen-antibody complexes were incubated with PE conjugated goat antibody to mouse IgG (Jackson) for detection (10 minutes).

All single cells were isolated from cell suspensions by micromanipulation. Bone marrow cells were plated at a density of 250,000 cells/0.8 cm$^2$ in a volume of 200 µl on a microscope slide. Single fluorescent cells were aspirated into a glass pipette of approximately 30 µm diameter and transferred to a new slide. After confirming that only a single cell had been transferred, this cell was finally picked in 1 μl pick buffer into the PCR-reaction tube.

Figure 4:
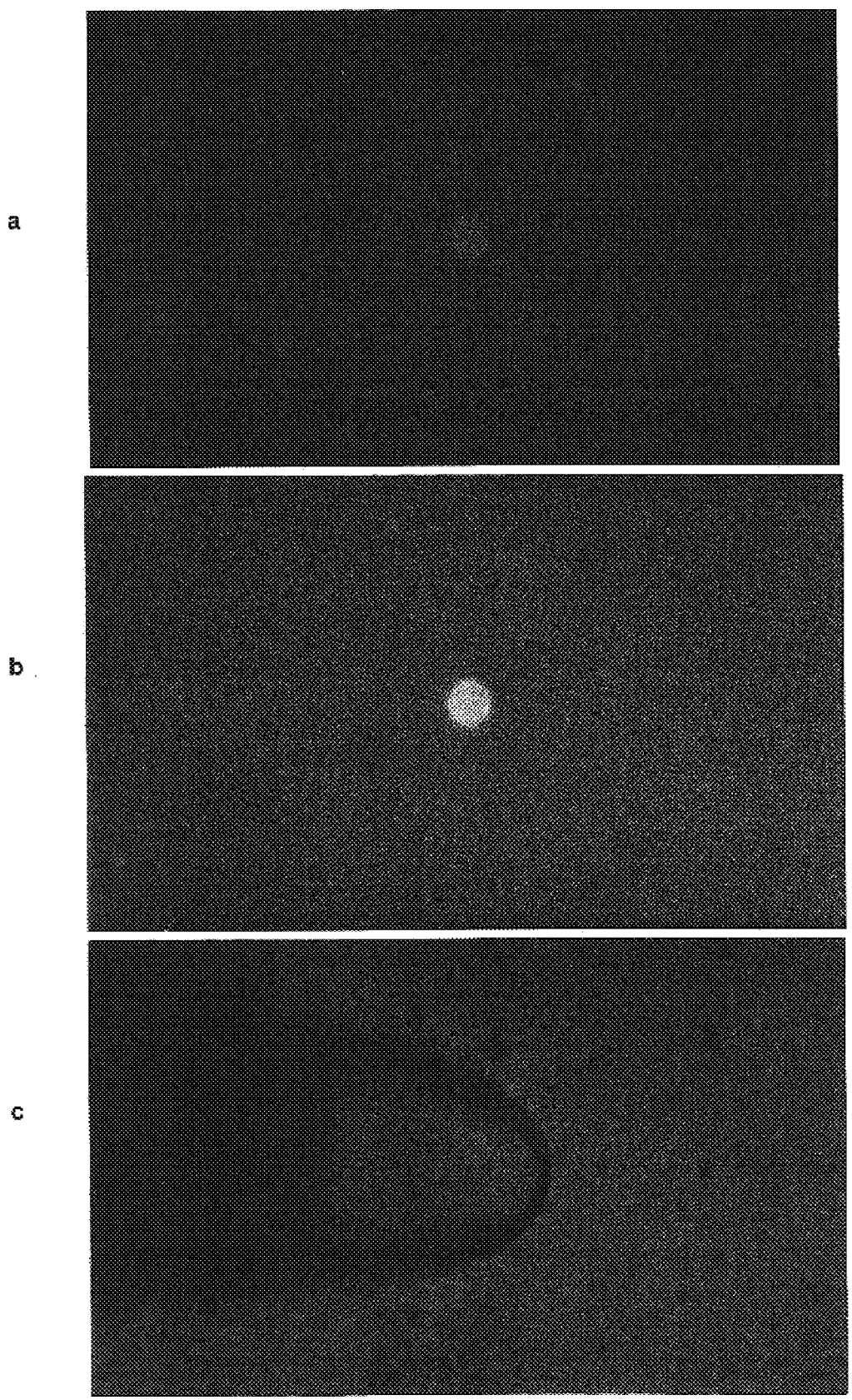
FIG. 4. Isolation of a single disseminated tumor cell from bone marrow of a breast cancer patient. After immunostaining, the cell suspension was pipetted onto a slide and checked for immunofluorescent cells (A). (B) demonstrates the bright cytoplasmic staining and that the surrounding cells do not show any background fluorescence. The cell was then aspirated by a glass capillary (C) and transferred to a new slide. No other than the fluorescent cell was transferred as the whole visual field did not contain any other cell. From there the cell was taken to the amplification tube. (D) depicts the chromosomal changes of the cell.
Figure 4D:
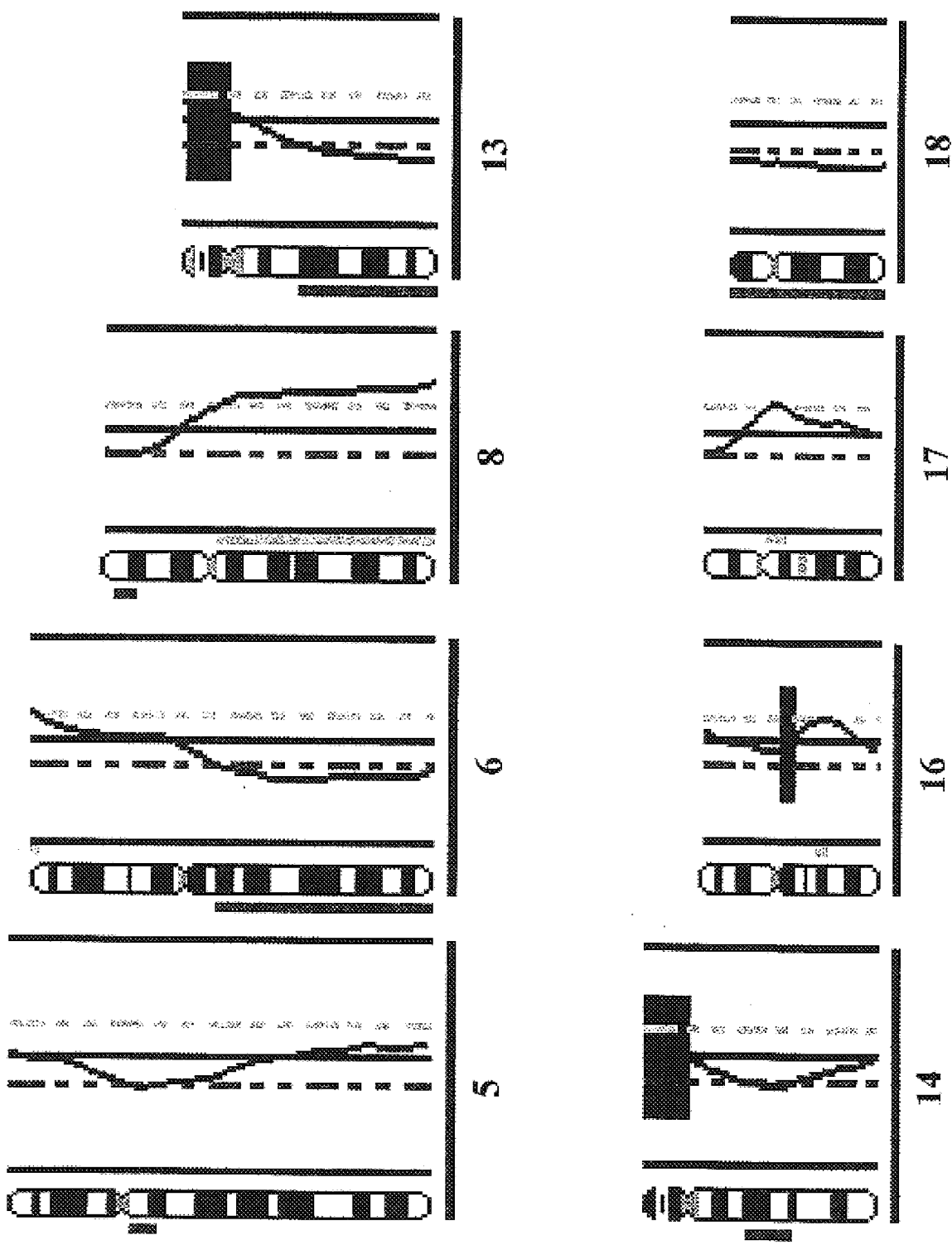

In the marrow aspirate from the pelvic bone of a patient, diagnosed with a primary breast cancer without evidence for distant metastasis, staged according to the international classification as pT3, pN1, pM0, pG3, a single immunofluorescence-labeled cell detected among unstained bone marrow cells, was picked by micromanipulation and transferred to a new slide for visual control that no additional cell was inadvertently aspirated (FIG. 4A–C). From this slide the cell was taken to the final reaction tube. FIG. 4D depicts the chromosomal gains and losses found by CGH analysis in this cell that were consistent with chromosomal imbalances reported earlier for breast cancer. For example, the observed amplifications on 8q and 17q represent two of the three most common gains while losses of 8p and 13q are also known to occur frequently in breast cancer (Forozan (1997), Trends Genet 13, 405–9).

EXAMPLE 7

CGH Analysis of a Tumor Cell From a Patient With CUP-syndrome

Figure 5:
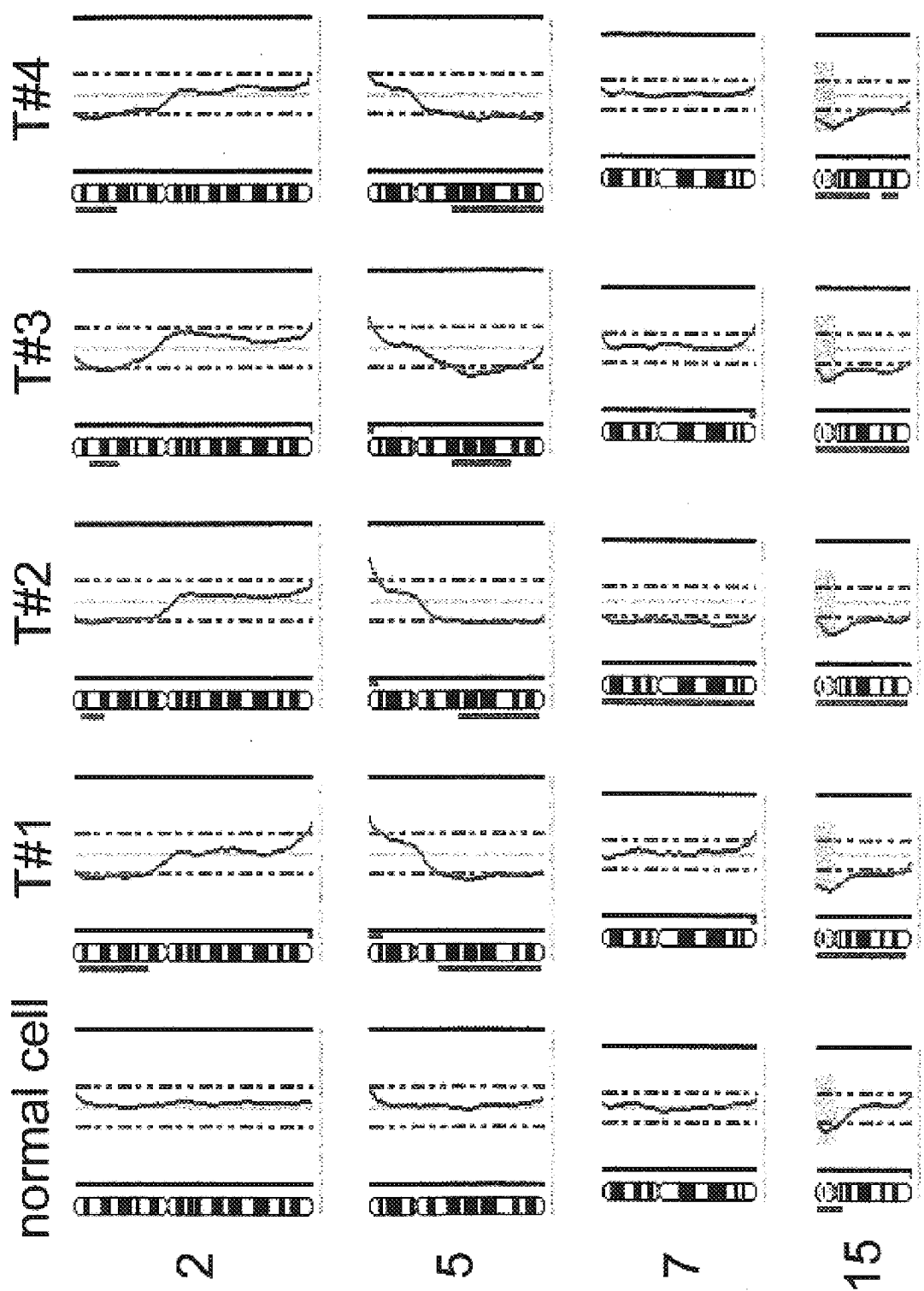
FIG. 5. CGH-profile of four single tumor cells (T#1–T#4) and one normal cell of a patient with CUP-syndrome. Chromosomes 2, 5, 7 and 15 are chosen for comparison of identical and divergent findings. The losses on chromosomes 2, 5 and 15 are common for all tumor cells whereas the loss of chromosome 7 was only seen for T#2. As in the other profiles, chromosomal losses are marked by vertical bars at the left side of the chromosome symbol.

The same procedure as in Example 6 was applied to four individual cytokeratin-positive tumor cells and four unstained control cells isolated from the bone marrow of a patient with a cancer of unknown primary lesion (CUP-syndrome), who was initially presented with liver metastasis. The findings of the CGH analysis of the four tumor cells, summarized in FIG. 5 and in Table 3, showed a remarkable congruent pattern of genomic changes (Table 3). Particularly the distinct loss of the so-called consensus deletion regions-3p, 5q, 10q, 13q, and 17p-, suggested that the cytokeratin-positive cells originated from a small cell lung cancer (Ried (1994), Cancer Res 54, 1801–6). Clinical imaging of a characteristic pulmonary lesion and histopathological examination of a metastasis led to the diagnosis of a "small to intermediate cell—most likely epithelial—tumor"—thus corroborating CGH based suspicion.

TABLE 3

Summary of the CGH results of four individual cytokeratin-positive cells isolated from the bone marrow of a patient with CUP-syndrome. Some deviations from the central line did not reach significance, but were very similar in their profile to the other tumor cells with significant changes as opposed to the control cell at the respective locus. These are given in parentheses. Changes unique to one cell are in bold letters.

| tumor cell # | chromosomal gains | chromosomal losses |
| --- | --- | --- |
| 1 | 8 q | 2 p, 3 p, 5 q, (8 p), 10, 13, 15, 16 q, 17 p, 22, Y |
| 2 | (8 q) | 2 p, 3 p, 5 q, 7, 8 p, 10, 13, 15, 16 q, 17 p, 22, Y |
| 3 | 8 q | 2 p, 3 p, 5 q, (8 p), 10, 13, 15, 16 q, 17 p, 22, Y |
| 4 | 8 q | 2 p, 3 p, 5 q, 8 p, 10, 13, 15, 16 q, 17 p, 22, Y |

EXAMPLE 8

Loss of Heterozygosity-analysis

In order to detect loss of heterozygosity and mutations in epithelial tumors, the amplified DNA of all four tumor cells from the patient with CUP syndrome (see Example 7) and the four unstained bone marrow cells were examined for the presence of loss of heterozygosity (LOH) and mutations. The detection of LOH in a single cell requires that the two allelic DNA strands are cut, ligated to the adaptor and amplified in a nearly identical fashion. For LOH analysis of the APC tumor suppressor gene on 5q21, the dinucleotide repeat polymorphism D5S346 located 40 kb downstream of the gene and a polymorphic AIw21I site located within exon 15 were used (Groden (1991), Cell 66, 589–600). The D16S3019 marker tightly linked the E-cadherin gene (Guilford (1998), Nature 392, 402–5) on 16q22 was applied to assess LOH of E-cadherin. Since the CGH results of the respective chromosomes already suggested a loss of chromosomal material from 5q and 16q, amplification of two alleles from each control cell and one from each tumor cell was calculated to result in 12 fragments (4×2 for the normal cells and 4×1 for the tumor cells) for each of the three markers, adding up to 36 independently amplified fragments. As it is depicted for APC in FIG. 6A, both alleles could be amplified from three of the four control cells for each of the two markers analyzed. The primary PCR-products were diluted 1:5 in $H_2O$. 1 μl of this dilution was used in the specific PCR. This specific PCR was carried out under standard primer conditions and the sequence of the D16S3019 locus, the D5S346 locus, the APC PCR-RFLP and the exons 2–9 of the p53 gene (Futeral (1991), Nucleic Acids Res. 19, 6977). Gel conditions for microsatellite analysis was performed as described in Litt (1993), Biotechniques 15, 280–4, and developed by incubation with SYBR-Green followed by fluorimaging. Analysis of the APC PCR-RFLP was performed by digesting 5 μl of the PCR products in a volume of 30 μl with 15 U AIw21I (MBI Fermentas) for 3h. The result was visualized in an ethidium bromide stained agarose gel.

Figure 6A:
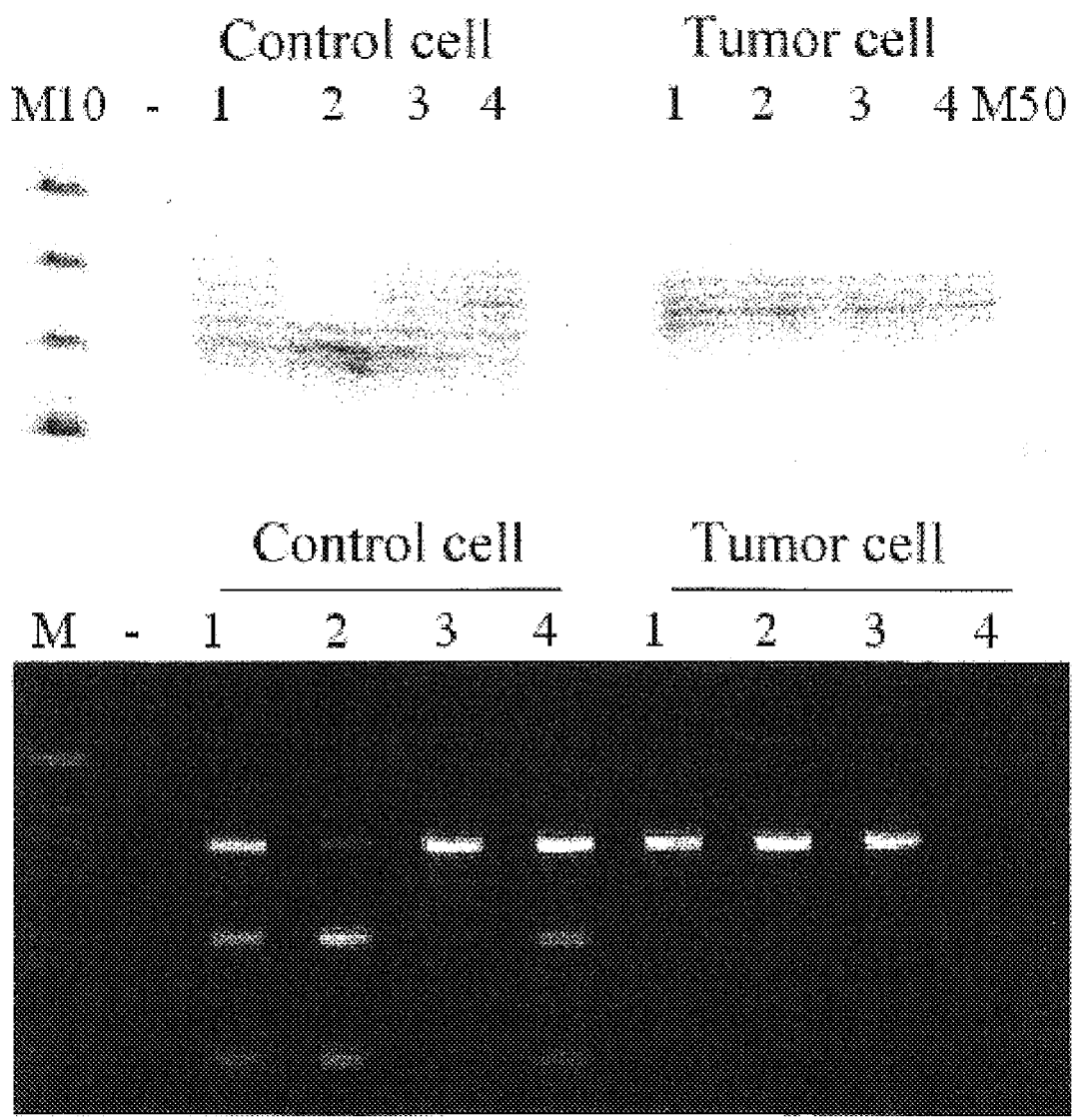
FIG. 6. (A) LOH-analysis using the dinucleotide repeat polymorphism at D5S346 locus linked to the APC gene (upper part) and PCR-RFLP of a Alw21I site within exon 15 of the APC gene (lower part). In the first experiment all four tumor cells demonstrate loss of one allele, whereas the single control cells contained two alleles except for #2. In the APC PCR-RFLP experiment all but one control cell (#3) had two alleles, whereas the tumor cells only contained the uncut fragment. The fragment of tumor cell #4 was not amplified (–, negative control; M10, 10 bp ladder; M50, 50 bp ladder; M, marker for agarose gel electrophoresis).

While the losses found in control cell #2 and #3 were not seen with the second marker, all tumor cells showed LOH in both experiments. Similar results were obtained for E-cadherin: all control cells were informative and showed two alleles whereas all four tumor cells had lost one allele. Taken together, 33 of the 36 expected fragments were amplified and detected. These data not only demonstrate a respectable reliability of the method but also indicate that a presumed loss needs to be controlled by additional markers (FIG. 6A).

Figure 6B:
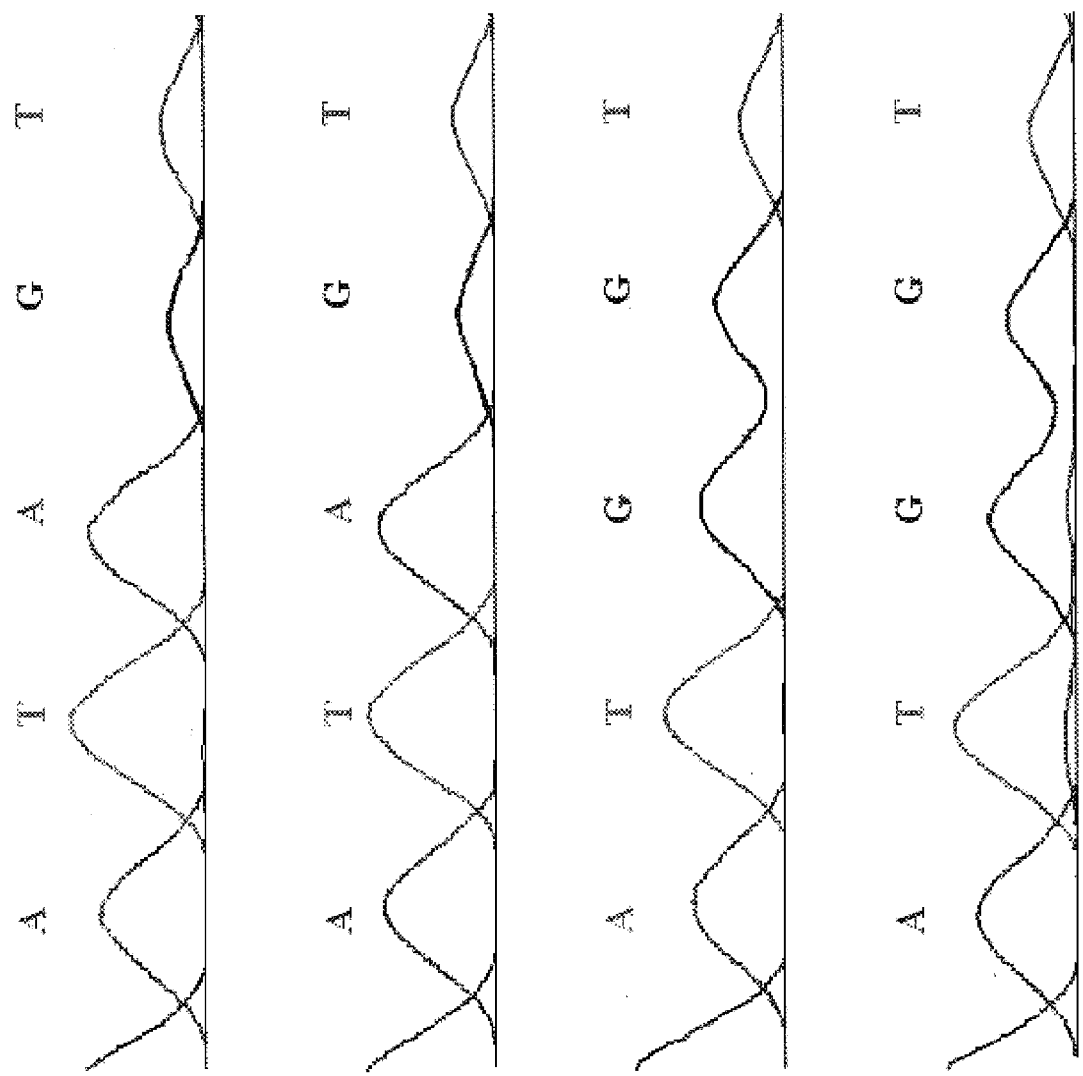

In order to avoid Taq polymerase errors during the early cycles the PCR, a mixture of Taq polymerase with a proof-reading enzyme, Pwo polymerase was used. Because the CGH-profiles of all four tumor cells showed a loss of 17p, it was examined whether the remaining allele of the p53 tumor suppressor gene had been inactivated by a mutation. Mutations in p53, the most commonly mutated tumor suppressor gene in human cancer, occur in about 50% of lung carcinomas (Greenblatt (1994), Cancer Res. 54, 4855–78). Since the vast majority of mutations are localized within the core domain, exon 4–9 was amplified for sequencing. Successful amplification of all exons proved that the primary PCR conditions are sufficiently robust to yield products at least as large as 1374 bp, despite the presence of much smaller fragments. There are no MseI sites contained within these exons, a prerequiste for successful amplification. The map of MseI cleavage sites in the p53 gene region predicted four exon containing fragments: one of 1374 bp with exons 2, 3 and 4, another of 1032 bp with exons 5 and 6, a third of a 722 bp fragment with exon 7, and a fourth of a 558 bp with exons 8 and 9. Sequencing of all four tumor cells showed an A→G mutation in codon 215 of p53, leading to a serine to glycine exchange, which had already been described in several human cancers before (Hainaut (1998), Nucleic Acids Res. 26, 205–13). Four normal bone marrow cells contained the wild-type sequence at codon 215 (FIG. 6B) of p53, virtually excluding that a Taq polymerase error accounted for the A→G mutation. No other deviation from the wild type sequence was found in the exons of tumor and control cell DNA, indicating that Taq polymerase induced mutations are rather rare under the applied conditions.

EXAMPLE 9

DNA Sequence Analysis by Direct Sequencing and SSCP

After detection of said A→G mutation in codon 215 of p53, it was tested whether it would be possible to detect said point mutations by single strand conformation polymorphism (SSCP). Single strand conformation polymorphism relies on the principle that single stranded DNA strands of different sequences exhibit different mobilities during electrophoresis in non-denaturing polyacrylamid gels. The strategy of the method is to amplify the segment of interest of a gene by PCR and then to compare the mobility of the denatured DNA with that of a reference segment of known sequence. Single point mutations within a sequence already lead to changed running behaviour in the gel, this method is very well suited for detecting the presence of mutations in a segment of DNA. Under non-denaturing conditions single stranded DNA exhibits a folded structure, which is determined essentially by intramolecular interactions and thus by the sequence. The occurrence of mutational changes in the DNA sequence causes a changed folded structure. Thus, in the SSCP analysis the detection of a mutated sequence is determined by the changed mobility in the polyacrylamid gel electrophoresis. The method has to be adjusted for sensitivity for each fragment to be analyzed. Important variables are the length of the fragment, ideally between 120–350 bp, and the temperature of the gel run. Once established SSCP has the advantage of screening a high number of probes at the same time without expensive and laborious sequencing. However, a fragment with a changed running behaviour should subsequently sequenced in order to name the mutation.

In this experiment, the running behavior of three single cytokeratin-negative cells from the patient with CUP syndrome and the cancer cells that had already been sequenced was compared. The mutation could be picked up in all cytokeratin-positive cells, whereas the normal cells did not show a changed mobility, as demonstrated in FIG. 7.

EXAMPLE 10

CGH of Laser-microdissected Single Cells

Analysis of many clinical samples requires the isolation of the cells of interest from the surrounding tissue. It was tested whether the procedure also works in the setting of laser assisted microdissection. In one of the more advanced techniques laser microbeam microdissection (LMM) is combined with laser pressure catapulting (LPC): the cells are cut out and subsequently catapulted into the tube. To avoid the introduction of confounding variables such dissected nuclei cytospins of normal leukocytes were prepared and then isolated the single cells by LMM and LPC. The DNA preparation and CGH was performed as in examples 1–3 and results were as expected: The profiles were normal for normal cells demonstrating that the method is applicable to microdissected single cells the same way as to cells isolated from suspensions.

EXAMPLE 11

Isolation of Single Disseminated Tumor Cells From Lymph Nodes

Lymphogenic metastasis is a very important way for tumor cells to disseminate and often determines the prognosis of the patient. Immunohistochemically/immunocytochemically detectable disseminated tumor cells have been shown to predict the patients outcome in a variety of studies. The genetic changes of these cells have not yet been characterized so far. Cell suspensions from lymph nodes were prepared and tested the application of the present invention. Cell suspensions were prepared using the Medi-Machine from Biorad according to the manufacturer's instructions. Tumor cells were detected by staining with the mab Ber-EP4 from Dako that recognizes the EpCAM epitope and has been shown to be even more specific in lymph nodes than cytokeratin antibodies. Stained cells were isolated and the single cell DNA prepared as mentioned. Then, CGH was performed. Normal, unstained cells demonstrated normal profiles and in tumor cells a variety of aberrations could be detected.

EXAMPLE 12

Isolation of Single Circulating Tumor Cells From Peripheral Blood

In analogy to the analysis of disseminated tumor cells isolated from bone marrow and lymph nodes it was also looked for cells in the peripheral blood of patients with malignant disease. Peripheral blood cells of carcinoma patients were screened with the cytokeratin antibody A45 B/B3, of a melanoma patient with the mab 9.2.27 (from R. Reisfeld, San Diego, USA) directed against the human melanoma associated chondroitin sulfate proteoglycan (MCSP). The blood of a B-CLL patient was screened with an antibody directed against CD24 (antibody from Cymbus Biotechnology, CBL478). The method worked equally well as with cells isolated from bone marrow and lymph node.

EXAMPLE 13

Isolation and Characterization of Single Hb-F Positive Cells

Circulating cells from the child can be detected in the venous blood of the mother during pregnancy and also up to 27 years postpartum, as demonstrated in one study (Bianchi (1996), P.N.A.S. USA 93, 705–709). During pregnancy these cells could be useful for prenatal diagnosis without any danger for the mother and the child. The persistent microchimerism in the mother has been connected to higher prevalence of autoimmune diseases in women. One way to detect these fetal cells is the use of antibodies to fetal hemoglobin (Hb-F) for the detection of erythroblasts. This antibody (mouse mab to Hb-F: Coltag, Cat. No. MHFHOO) was used to detect erythroblasts in umbilical cord blood of a newborn. Single cells were isolated and the methods applied as described. The CGH profiles were normal for all chromosomes. The boy was healthy, as demonstrated in FIG. 8.

EXAMPLE 14

Fingerprints of Single Cells

The reliability of amplification for a sequence that is only once present in a genome was shown in a large number of experiments to be 90%. This is an important value for the analysis of loss of heterozygosity. However, for fingerprint analysis it is not only important that the sequences are reliably amplified but also that a polymorphism can be identified. In order to test this, the band sizes obtained from a PCR reaction with 3000 cells with those from a single cell were compared. It was detected that—within the known limits of the microsatellite analysis—the bands showed no altered migration behaviour as compared to the positive control. This is demonstrated in FIG. 9. Therefore, the polymorphic bands can be identified and fingerprints be obtained from single cells.

EXAMPLE 15

Isolation of Single Enzymatically Stained Cells For Routine and Diagnostic Procedures For many diagnostic and routine uses it is advantageous to avoid immunofluorescence. Ways to prepare cells for experiments that imply routine light microscopy were tested. The first experiments tested which enzymatic staining reaction with alkaline phosphatase can be applied without damaging the DNA. Several commercially available substrates of alkaline phosphatase were tested, such as different preparations of Neufuchsin and BCIP/NBT (Biorad). Only single cells stained with BCIP/NBT were successfully amplified. In a next step, intact cells were isolated from routine slides. For doing so, cells in PBS were pipetted on special positively charged slides (Menzel), where they adhered within 30 minutes, the PBS was discarded and the slide were air-dried. After this treatment routine staining procedures such as the APAAP technique (alkaline phosphatase-anti-alkaline phosphatase technique) with BCIP/NBT development can be applied. Addition of a non-ionic detergent to PBS later helps to overcome the adhesive forces during the micromanipulation for isolation of the stained cells. Results of these experiments are demonstrated in FIG. 10.

All CGH-, LOH- and SSCP-experiments, i.e. with normal cells from peripheral blood, tumor cells from bone marrow, blood and lymph node, stained with cytokeratine ab, Ber-EP4 and anti-Hb-F have also been performed using this procedure giving equally excellent results.

EXAMPLE 16

Application of the Method of the Invention to Single Cells of Various Sources In summary, it can be stated that the method of the invention works independently of the source of tissue from which the cell is derived, of the antibody used to detect the rare cell within a cell population or environment and/or of the choice of labeling, i.e. fluorescent dyes or enzymatically activated substrates such as BCIP/NBT (see Table 4).

TABLE 4

Application of single cell PCR to individual cells from different tissues and diagnostic settings

| Sample | PCR analysis (Analytical PCR, LOH, SSCP, fingerprint or sequencing) | CGH analysis |
|---|---|---|
| Normal PBL | 60 | 10 |
| PBL with trisomy 21 | 4 | 2 |
| Hb-F positive PBL | 10 | 10 |
| Laser-microdissected PBL | 2 | 2 |
| Tumor cells from BM of carcinomas patients: | | |
| Breast cancer | 140 | 69 |
| Prostate cancer | 17 | 9 |
| Gastric cancer | 6 | |
| Colon cancer | | |
| Pancreatic cancer | 17 | |
| Oesophageal cancer | 2 | |
| Lung cancer | 8 | |
| CUP | 16 | 8 |
| Cervix | 6 | 3 |
| Tumor cells from LN of carcinoma patients: | | |
| Gastric | 21 | |
| Colon | 11 | |
| Lung | 4 | |
| Tumor cells from peripheral blood of carcinoma patients | | |
| Breast | 3 | 2 |
| Cervix | 3 | 1 |
| Lung | 7 | |
| Tumor cells from peripheral blood of non-epithelial malignancies | | |
| Melanoma | 5 | 1 |
| B-CLL | 5 | 2 |
| M. Hodgkin | 1 | |

BM = bone marrow;
LN = lymph node

---

What is claimed is:

1. A method for the amplification of DNA comprising:
   (a) providing a sample comprising DNA;
   (b) digesting the DNA to be amplified with a restriction endonuclease under conditions suitable to obtain DNA fragments of similar length, wherein said restriction endonuclease is capable of providing 5' overhangs wherein the terminal nucleotide of the overhang is phosphorylated or 3' overhangs wherein the terminal nucleotide of the overhang is hydroxylated on said DNA fragments;
   (c) annealing at least one primer to said DNA fragments and further performing steps selected from the group consisting of
      (i) hybridizing, simultaneously or subsequently, oligonucleotides representing a first primer to said 5' overhangs on said DNA fragments of step (b), and further hybridizing oligonucleotides representing a second primer to 3' overhangs generated by said first primer, wherein said first and second primer are of different lengths; ligating said second primer to said 5' overhangs; and removing said first primer from said DNA fragments;
      (ii) hybridizing, simultaneously or subsequently, oligonucleotides representing a first primer, wherein the nucleotide at the 5' terminus is phosphorylated, to said 5' overhangs on said DNA fragments of step (b), and further hybridizing oligonucleotides representing a second primer with said first primer; and ligating said first and second primer to said DNA fragments; and
      (iii) hybridizing oligonucleotides representing said primer to said 3' overhangs so that 5' overhangs are generated; and ligating said primer to recessed 5' ends of said DNA fragments;
   (d) filling in generated 5' overhangs; and
   (e) amplifying said DNA fragments with primers which are capable of hybridizing with the complementary strand of said primer(s) of step (c) to obtain said amplified DNA.

2. The method of claim 1, wherein said DNA is the genome of a single cell or of chromosomes or of (a) fragment(s) thereof.

3. The method of claim 2, wherein said single cell is a disseminated tumor cell, a peripheral blood cell, a cell from bone marrow aspirates, a cell from tumor biopsy, a cell obtained from umbilical cord blood, a cell obtained from a lymph node or a cell obtained from microdissected tissue.

4. The method of claim 1, wherein said DNA is present in the form of one copy of a double stranded DNA sequence.

5. The method of claim 1, wherein the relative numerical abundance of said DNA fragments is maintained.

6. The method of claim 1, wherein prior to step (a), said sample comprising said DNA is digested with a proteinase, and wherein after the protein is digested, the proteinase is inactivated.

7. The method of claim 6, wherein said proteinase is thermo-labile.

8. The method of claim 6, wherein said proteinase is Proteinase K.

9. The method of claim 6, wherein said proteinase is thermally inactivated.

10. The method of claim 1, wherein said DNA fragments have a size of <3 kbp.

11. The method of claim 1, wherein said DNA fragments have an average length of about 200–400 bp.

12. The method of claim 1, wherein said restriction site recognized by said restriction endonuclease does not comprise a cytosine or a guanine.

13. The method of claim 1, wherein said restriction endonuclease recognizes a motif with four defined bases.

14. The method of claim 1, wherein said restriction endonuclease recognizes the consensus sequence TTAA.

15. The method of claim 1, wherein said restriction endonuclease is MseI or an isoschizomer thereof.

16. The method of claim 1, wherein in step (i) said second primer is longer than said first primer.

17. The method of claim 16, wherein in step (c) the annealing temperature of said second primer is higher than the hybridizing temperature of said first primer to said second primer and said 5' overhangs.

18. The method of claim 1, wherein in step (i) said first primer comprises 11 or 12 nucleotides and said second primer comprises 21 nucleotides.

19. The method of claim 1, wherein in step (i) or step (ii) said first primer is at least partially complementary to said second primer.

20. The method of claim 1, wherein the sequence of said first and said second primer is non-degenerate.

21. The method of claim 1, wherein said first primer used in step (i) comprises SEQ ID NO: 2 and wherein said second primer used in step (i) comprises SEQ ID NO: 1.

22. The method of claim 1, wherein said first primer and said second primer are hybridized to each other separately from said DNA fragments and are added to said DNA fragments prior to step (i) or step (ii).

23. The method of claim 1, wherein the last 3' nucleotide of the first primer in step (i) is a ddNTP.

24. The method of claim 2, wherein essentially the whole nuclear genome of said single cell is amplified.

25. The method of claim 2, wherein said single cell is a chemically fixed cell.

26. The method of claim 1, wherein steps (a) to (e) are carried out in one reaction vessel.

27. The method of claim 1, wherein said first primer used in step (i) comprises SEQ ID NO:2.

28. The method of claim 1, wherein said second primer used in step (i) comprises SEQ ID NO:1.

29. A method of claim 1 further comprising:
   (f) performing an analysis on said amplified DNA of step(e).

30. The method of claim 29, wherein said analysis is selected from the group consisting of comparative genomic hybridization (CGH), representational difference analysis (RDA), analytical PCR, restriction fragment length polymorphism analysis (RFLP), single strand conformation polymorphism analysis (SSCP), DNA sequence analysis, "loss of heterozygosity" analysis (LOH), fingerprint analysis, fluorescence in siru hybridization (FISI) and a combination thereof.

* * * * *